US009351705B2

(12) United States Patent
Wang et al.

(10) Patent No.: US 9,351,705 B2
(45) Date of Patent: May 31, 2016

(54) MINIATURIZED PHOTOACOUSTIC IMAGING APPARATUS INCLUDING A ROTATABLE REFLECTOR

(75) Inventors: Lihong Wang, Creve Coeur, MO (US); Konstantin Maslov, Affton, MO (US); Joon-Mo Yang, St. Louis, MO (US)

(73) Assignee: Washington University, St. Louis, MO (US)

( * ) Notice: Subject to any disclaimer, the term of this patent is extended or adjusted under 35 U.S.C. 154(b) by 1114 days.

(21) Appl. No.: 13/143,832

(22) PCT Filed: Jan. 8, 2010

(86) PCT No.: PCT/US2010/020488
§ 371 (c)(1),
(2), (4) Date: Jul. 8, 2011

(87) PCT Pub. No.: WO2010/080991
PCT Pub. Date: Jul. 15, 2010

(65) Prior Publication Data
US 2011/0275890 A1      Nov. 10, 2011

Related U.S. Application Data

(60) Provisional application No. 61/143,668, filed on Jan. 9, 2009.

(51) Int. Cl.
*A61B 8/08* (2006.01)
*A61B 8/00* (2006.01)
(Continued)

(52) U.S. Cl.
CPC ............. *A61B 8/4461* (2013.01); *A61B 5/0062* (2013.01); *A61B 5/0084* (2013.01); *A61B 5/0095* (2013.01); *A61B 8/12* (2013.01); *A61B 5/08* (2013.01)

(58) Field of Classification Search
CPC ............................ A61B 5/0095; A61B 8/5207
See application file for complete search history.

(56) References Cited

U.S. PATENT DOCUMENTS 4,029,756 A    6/1977   Gaafar
4,127,318 A    11/1978  Determann et al.
(Continued)

FOREIGN PATENT DOCUMENTS

EP          0012262 A1    6/1980
EP          1 493 380 A1  1/2005
(Continued)

OTHER PUBLICATIONS

G. J. Tearney, et al., Scanning Single-Mode Fiber Optic Catheter-Endoscope for Optical Coherence Tomography, Optics Letters pp. 543-545, vol. 21, No. 7, 1996, Optical Society of America.
(Continued)

*Primary Examiner* — Joel Lamprecht
(74) *Attorney, Agent, or Firm* — Armstrong Teasdale LLP

(57) ABSTRACT

A reflection-mode photoacoustic endoscope includes a light source configured to emit a light pulse, a signal detection or transmission unit configured to detect or emit an ultrasonic pulse, and a rotatable reflector. The rotatable reflector is configured to reflect at least one of the light pulse and the ultrasonic pulse into a target area of an object, and reflect a response signal to the signal detection unit. The response signal is one of a photoacoustic wave generated by the object responsive to the light pulse and an ultrasonic pulse echo generated by the object responsive to the ultrasonic pulse.

20 Claims, 11 Drawing Sheets

(51) Int. Cl.
  *A61B 5/00* (2006.01)
  *A61B 8/12* (2006.01)
  *A61B 5/08* (2006.01)

(56) References Cited

U.S. PATENT DOCUMENTS

| | | | |
|---|---|---|---|
| 4,255,971 A | 3/1981 | Rosencwaig | |
| 4,267,732 A | 5/1981 | Quate | |
| 4,375,818 A | 3/1983 | Suwaki et al. | |
| 4,385,634 A | 5/1983 | Bowen | |
| 4,430,897 A | 2/1984 | Quate | |
| 4,462,255 A | 7/1984 | Guess et al. | |
| 4,468,136 A | 8/1984 | Murphy et al. | |
| 4,489,727 A | 12/1984 | Matsuo et al. | |
| 4,546,771 A * | 10/1985 | Eggleton et al. | 600/437 |
| 4,596,254 A | 6/1986 | Adrian et al. | |
| 4,740,081 A | 4/1988 | Martens et al. | |
| 4,802,461 A | 2/1989 | Cho | |
| 4,802,487 A | 2/1989 | Martin et al. | |
| 4,809,703 A | 3/1989 | Ishikawa et al. | |
| 4,850,363 A | 7/1989 | Yanagawa | |
| 4,860,758 A | 8/1989 | Yanagawa et al. | |
| 4,869,256 A | 9/1989 | Kanno et al. | |
| 4,921,333 A | 5/1990 | Brody et al. | |
| 4,995,396 A | 2/1991 | Inaba et al. | |
| 5,070,455 A | 12/1991 | Singer et al. | |
| 5,083,549 A | 1/1992 | Cho et al. | |
| 5,107,844 A | 4/1992 | Kami et al. | |
| 5,115,814 A | 5/1992 | Griffith et al. | |
| 5,125,410 A | 6/1992 | Misono et al. | |
| 5,140,463 A | 8/1992 | Yoo et al. | |
| 5,170,793 A | 12/1992 | Takano et al. | |
| 5,207,672 A | 5/1993 | Roth et al. | |
| 5,227,912 A | 7/1993 | Ho et al. | |
| 5,305,759 A | 4/1994 | Kaneko et al. | |
| 5,320,106 A * | 6/1994 | Tanaka | 600/463 |
| 5,321,501 A | 6/1994 | Swanson et al. | |
| 5,331,466 A | 7/1994 | Van Saarloos | |
| 5,345,938 A | 9/1994 | Nishiki et al. | |
| 5,373,845 A | 12/1994 | Gardineer et al. | |
| 5,414,623 A | 5/1995 | Lu et al. | |
| 5,445,155 A | 8/1995 | Sieben | |
| 5,465,722 A | 11/1995 | Fort et al. | |
| 5,546,947 A | 8/1996 | Yagami et al. | |
| 5,546,948 A | 8/1996 | Hamm et al. | |
| 5,606,975 A | 3/1997 | Liang et al. | |
| 5,615,675 A | 4/1997 | O'Donnell et al. | |
| 5,635,784 A | 6/1997 | Seale | |
| 5,651,366 A | 7/1997 | Liang et al. | |
| 5,713,356 A | 2/1998 | Kruger | |
| 5,718,231 A | 2/1998 | Dewhurst et al. | |
| 5,836,872 A | 11/1998 | Kenet et al. | |
| 5,840,023 A | 11/1998 | Oraevsky et al. | |
| 5,860,934 A | 1/1999 | Sarvazyan | |
| 5,913,234 A | 6/1999 | Julliard et al. | |
| 5,971,998 A | 10/1999 | Russell et al. | |
| 5,991,697 A | 11/1999 | Nelson et al. | |
| 6,055,097 A | 4/2000 | Lanni et al. | |
| 6,102,857 A | 8/2000 | Kruger | |
| 6,104,942 A | 8/2000 | Kruger | |
| 6,108,576 A | 8/2000 | Alfano et al. | |
| 6,111,645 A | 8/2000 | Tearney et al. | |
| 6,134,003 A | 10/2000 | Tearney et al. | |
| 6,216,025 B1 | 4/2001 | Kruger | |
| 6,233,055 B1 | 5/2001 | Mandella et al. | |
| 6,282,011 B1 | 8/2001 | Tearney et al. | |
| 6,292,682 B1 | 9/2001 | Kruger | |
| 6,309,352 B1 | 10/2001 | Oraevsky et al. | |
| 6,341,036 B1 | 1/2002 | Tearney et al. | |
| 6,379,325 B1 | 4/2002 | Benett et al. | |
| 6,405,069 B1 | 6/2002 | Oraevsky et al. | |
| 6,413,228 B1 | 7/2002 | Hung et al. | |
| 6,421,164 B2 | 7/2002 | Tearney et al. | |
| 6,432,067 B1 | 8/2002 | Martin et al. | |
| 6,466,806 B1 | 10/2002 | Geva et al. | |
| 6,485,413 B1 | 11/2002 | Boppart et al. | |
| 6,490,470 B1 | 12/2002 | Kruger | |
| 6,498,942 B1 | 12/2002 | Esenaliev et al. | |
| 6,498,945 B1 | 12/2002 | Alfheim et al. | |
| 6,501,551 B1 | 12/2002 | Tearney et al. | |
| 6,564,087 B1 | 5/2003 | Pitris et al. | |
| 6,567,688 B1 | 5/2003 | Wang | |
| 6,626,834 B2 | 9/2003 | Dunne et al. | |
| 6,633,774 B2 | 10/2003 | Kruger | |
| 6,654,630 B2 | 11/2003 | Zuluaga et al. | |
| 6,658,279 B2 | 12/2003 | Swanson et al. | |
| 6,694,173 B1 | 2/2004 | Bende et al. | |
| 6,701,181 B2 | 3/2004 | Tang et al. | |
| 6,751,490 B2 | 6/2004 | Esenalieve et al. | |
| 6,764,450 B2 | 7/2004 | Yock | |
| 6,831,781 B2 | 12/2004 | Tearney et al. | |
| 6,833,540 B2 | 12/2004 | MacKenzie et al. | |
| 6,839,496 B1 | 1/2005 | Mills et al. | |
| 6,846,288 B2 | 1/2005 | Nagar et al. | |
| 6,877,894 B2 | 4/2005 | Vona et al. | |
| 6,937,886 B2 | 8/2005 | Zavislan | |
| 6,956,650 B2 | 10/2005 | Boas et al. | |
| 7,072,045 B2 | 7/2006 | Chen et al. | |
| 7,198,778 B2 | 4/2007 | Achilefu et al. | |
| 7,231,243 B2 | 6/2007 | Tearney et al. | |
| 7,245,789 B2 | 7/2007 | Bates et al. | |
| 7,266,407 B2 | 9/2007 | Li et al. | |
| 7,322,972 B2 | 1/2008 | Viator et al. | |
| 7,357,029 B2 | 4/2008 | Falk | |
| 7,382,949 B2 | 6/2008 | Bouma et al. | |
| 7,917,312 B2 | 3/2011 | Wang et al. | |
| 8,016,419 B2 | 9/2011 | Zhang et al. | |
| 8,025,406 B2 | 9/2011 | Zhang et al. | |
| 8,397,573 B2 | 3/2013 | Kobayashi | |
| 8,416,421 B2 | 4/2013 | Wang et al. | |
| 8,454,512 B2 | 6/2013 | Wang et al. | |
| 8,764,666 B2 * | 7/2014 | Chen et al. | A61B 5/0062 600/310 |
| 2001/0052979 A1 | 12/2001 | Treado et al. | |
| 2002/0176092 A1 | 11/2002 | Deck | |
| 2003/0097066 A1 | 5/2003 | Shelby et al. | |
| 2003/0160957 A1 | 8/2003 | Oldham et al. | |
| 2003/0160967 A1 | 8/2003 | Houston et al. | |
| 2004/0039379 A1 | 2/2004 | Viator et al. | |
| 2004/0082070 A1 | 4/2004 | Jones et al. | |
| 2005/0015002 A1 | 1/2005 | Dixon et al. | |
| 2005/0143664 A1 | 6/2005 | Chen et al. | |
| 2005/0154313 A1 | 7/2005 | Desilets et al. | |
| 2005/0217381 A1 | 10/2005 | Falk | |
| 2006/0055936 A1 | 3/2006 | Yun et al. | |
| 2006/0058614 A1 | 3/2006 | Tsujita | |
| 2006/0122516 A1 | 6/2006 | Schmidt et al. | |
| 2006/0181791 A1 | 8/2006 | Van Beek et al. | |
| 2006/0184042 A1 | 8/2006 | Wang et al. | |
| 2006/0235299 A1 * | 10/2006 | Martinelli | 600/434 |
| 2006/0264717 A1 | 11/2006 | Pesach et al. | |
| 2007/0088206 A1 | 4/2007 | Peyman et al. | |
| 2007/0213590 A1 * | 9/2007 | Squicciarini | 600/172 |
| 2007/0213618 A1 | 9/2007 | Li et al. | |
| 2007/0282200 A1 | 12/2007 | Johnson et al. | |
| 2007/0299341 A1 | 12/2007 | Wang et al. | |
| 2008/0088838 A1 | 4/2008 | Raicu et al. | |
| 2008/0173093 A1 | 7/2008 | Wang et al. | |
| 2008/0230717 A1 | 9/2008 | Ashkenazi et al. | |
| 2009/0024038 A1 * | 1/2009 | Arnold | A61B 5/0095 600/459 |
| 2009/0088631 A1 | 4/2009 | Dietz et al. | |
| 2009/0116518 A1 * | 5/2009 | Patel et al. | 372/23 |
| 2009/0138215 A1 | 5/2009 | Wang et al. | |
| 2010/0079768 A1 | 4/2010 | Wang et al. | |
| 2010/0245766 A1 | 9/2010 | Zhang et al. | |
| 2010/0245769 A1 | 9/2010 | Zhang et al. | |
| 2010/0245770 A1 | 9/2010 | Zhang et al. | |
| 2010/0249562 A1 | 9/2010 | Zhang et al. | |
| 2010/0268042 A1 | 10/2010 | Wang et al. | |
| 2010/0285518 A1 | 11/2010 | Viator et al. | |
| 2010/0309466 A1 | 12/2010 | Lucassen et al. | |
| 2011/0021924 A1 * | 1/2011 | Sethuraman et al. | 600/463 |
| 2011/0071402 A1 | 3/2011 | Masumura | |

(56) References Cited

U.S. PATENT DOCUMENTS

| | | | |
|---|---|---|---|
| 2011/0122416 A1 | 5/2011 | Yang et al. |
| 2011/0201914 A1 | 8/2011 | Wang et al. |
| 2011/0282181 A1 | 11/2011 | Wang et al. |
| 2011/0282192 A1 | 11/2011 | Axelrod et al. |
| 2012/0070817 A1 | 3/2012 | Wang et al. |
| 2012/0204648 A1 | 8/2012 | Wang et al. |
| 2012/0275262 A1 | 11/2012 | Song et al. |
| 2012/0307250 A1 | 12/2012 | Wang et al. |
| 2013/0199299 A1 | 8/2013 | Wang et al. |
| 2013/0245406 A1 | 9/2013 | Wang et al. |
| 2014/0009808 A1 | 1/2014 | Wang et al. |
| 2014/0142404 A1 | 5/2014 | Wang et al. |

FOREIGN PATENT DOCUMENTS

| | | | |
|---|---|---|---|
| JP | 05-126725 A | 5/1993 |
| JP | 2000292416 A | 10/2000 |
| JP | 2009-068977 A | 4/2009 |
| JP | 2010-017426 A | 1/2010 |
| WO | 2006/111929 A1 | 10/2006 |
| WO | 2007/148239 A2 | 12/2007 |
| WO | WO2008062354 A1 * | 5/2008 |
| WO | 2008100386 A2 | 8/2008 |
| WO | 2009/055705 A2 | 4/2009 |
| WO | 2010/048258 A1 | 4/2010 |
| WO | 2010/080991 A2 | 7/2010 |
| WO | 2011/091360 A2 | 7/2011 |
| WO | 2011/127428 A2 | 10/2011 |
| WO | 2013/086293 A1 | 6/2013 |

OTHER PUBLICATIONS

P. H. Tran, et al., In Vivo Endoscopic Optical Coherence Tomography by use of a Rotational Microelectromechanical System Probe, Optic Letters pp. 1236-1238, vol. 29, No. 11, 2004, Optical Society of America.
Z. Yaqoob, et al., Methods and Applications Areas of Endoscopic Optical Coherence Tomography, Journal of Biomedical Optics, pp. 063001-1 through 063001-19, vol. 11, No. 6, 2006.
J. A. Viator, et al, Design and testing of an Endoscopic Photoacoustic Probe for Determination of Treatment Depth after Photodynamic Therapy, SPIE Proceedings in Biomedical Optoacoustics II, pp. 16-27, 2001.
A. A. Oraevsky, et al., Laser Optoacoustic Tomography of Layered Tissues: Signal Processing, SPIE, pp. 59-70, vol. 2979, 1997.
S. Sethuraman, et al., Development of a Combined Intravascular Ultrasound and Photoacoustic Imaging System, Proc. SPIE, pp. 60860F-1 through 60860F-10, vol. 60860, 2006.
S. Sethuraman, et al., Intravascular Photoacoustic Imaging of Atherosclerotic Plaques: Ex Vivo Study Using a Rabbit Model of Atherosclerosis, Proc. SPIE pp. 643729-1 through 643729-9, vol. 643729, 2007.
Elena Savateeva, et al., Noninvasive Detection and Staging of Oral Cancer in Vivo with Confocal Optoacoustic Tomography, Proceedings of SPIE, pp. 55-66, vol. 3916, 2000, Biomedical Optoacoustics.
HC Yang, et al., Novel Biomedical Imaging that Combines Intravascular Ultrasound (IVUS) and Optical Coherence Tomography (OCT), Internataional Ultrasoncis Symposium Proceedings, pp. 1769-1772, 2008, IEEE.
Notification of Transmittal of the International Search Report and the Written Opinion of the International Searching Authority, or the Declaration, PCT/US2010/020488, dated Aug. 31, 2010, 11 pages.
Final Office Action from related U.S. Appl. No. 13/450,793 dated Nov. 22, 2013; 22 pgs.
Non-Final Office Action from related U.S. Appl. No. 13/450,793 dated Mar. 24, 2014; 22 pgs.
Siphanto et al., "Imaging of Small Vessels Using Photoacoustics: An In Vivo Study", Lasers in Surgery and Medicine, 2004, pp. 354-362, vol. 35.
Song et al., "Fast 3-D dark-field reflection-mode photoacoustic microscopy in vivo with a 30-MHz ultrasound linear array", Journal of Biomedical Optics, 2008, pp. 054028 1-054028 5, vol. 13, No. 5.

Song et al., "Section-illumination photoacoustic microscopy for dynamic 3D imaging of microcirculation in vivo", Optics Letters, 2010, pp. 1482-1484, vol. 35, No. 9.
Steinbrink et al., "Illuminating the BOLD signal: combined fMRI-fNIRS studies", Magnetic Resonance Imaging, 2006, pp. 495-505, vol. 24.
Stern, "In vivo evaluation of microcirculation by coherent light scattering", Nature, 1975, pp. 56-58, vol. 254.
Tam, "Applications of photoacoustic sensing techniques", Reviews of Modern Physics, 1986, pp. 381-431 and FIGS. 16, 26 and 32, vol. 58, No. 2.
Van Essen et al., "An Integrated Software Suite for Surface-based Analyses of Cerebral Cortex", Journal of the American Medical Informatics Association, 2001, pp. 443-459, vol. 8, No. 5.
Wang et al., "Ballistic 2-D Imaging Through Scattering Walls Using an Ultrafast Optical Kerr Gate", Science, 1991, pp. 769-771, vol. 253.
Wang et al., "MCML—Monte Carlo modeling of light transport in multi-layered tissues", Computer Methods and Programs in Biomedicine, 1995, pp. 131-146, vol. 47.
Wang et al., "Noninvasive laser-induced photoacoustic tomography for structural and functional in vivo imaging of the brain", Nature Biotechnology, 2003, pp. 803-806, vol. 21, No. 7.
Wang et al., "Three-dimensional laser-induced photoacoustic tomography of mouse brain with the skin and skull intact", Optics Letters, 2003, pp. 1739-1741, vol. 28, No. 19.
Wang et al., "Noninvasive photoacoustic angiography of animal brains in vivo with near-infrared light and an optical contrast agent", Optics Letters, 2004, pp. 730-732, vol. 29, No. 7.
Wang et al., "Biomedical Optics, Principles and Imaging", 2007, Wiley-Interscience, A John Wiley & Sons, Inc., Hoboken, New Jersey, US, 7 pgs.
Wang, "Multiscale photoacoustic microscopy and computed tomography", Nature Photonics, 2009, pp. 503-509, vol. 3.
Wang et al., "Intravascular Photoacoustic Imaging", IEEE Journal of Selected Topics in Quantum Electronics, 2010, pp. 588-599, vol. 16, No. 3.
Xu et al., "Photoacoustic imaging in biomedicine", Review of Scientific Instruments, 2006, pp. 041101 1-041101 22, vol. 77.
Xu et al., "Time Reversal Ultrasound Modulated Optical Tomography Using a BSO Phase Conjugate Mirror", poster presented at SPIE Conference 7177 on Jan. 26, 2009; 3 pgs.
Yadlowsky et al., "Multiple scattering in optical coherence microscopy", Applied Optics, 1995, pp. 5699-5707, vol. 34, No. 25.
Yang et al., "Optical coherence and Doppler tomography for monitoring tissue changes induced by laser thermal therapy—An in vivo feasibility study", Review of Scientific Instruments, 2003, pp. 437-440, vol. 74, No. 1.
Yao et al., "Monte Carlo simulation of an optical coherence tomography signal in homogeneous turbid media", Phys. Med. Biol., 1999, pp. 2307-2320, vol. 44.
Yodh et al., "Spectroscopy and Imaging With Diffusing Light", Physics Today, Mar. 1995, pp. 34-40.
Yodh et al., "Functional Imaging with Diffusing Light", Biomedical Photonics Handbook, 2003, Chapter 21, 45 pgs., CRC Press, Boca Raton.
Zeff et al., "Retinotopic mapping of adult human visual cortex with high-density diffuse optical tomography", Proceedings of the National Academy of Sciences, 2007, pp. 12169-12174, vol. 104, No. 29.
Zemp et al., "Realtime photoacoustic microscopy in vivo with a 30-MHz ultrasonic array transducer", Optics Express, 2008, pp. 7915-7928, vol. 16, No. 11.
Zhang et al., "Functional photoacoustic microscopy for high-resolution and noninvasive in vivo imaging", Nature Biotechnology, 2006, pp. 848-851, vol. 24, No. 7.
Zhang et al., "In vivo imaging of subcutaneous structures using functional photoacoustic microscopy", Nature Protocols, 2007, pp. 797-804, vol. 2, No. 4.
Zhang et al., "Intrinsic Functional Relations Between Human Cerebral Cortex and Thalamus", J Neurophysiol, 2008, pp. 1740-1748, vol. 100.

(56) References Cited

OTHER PUBLICATIONS

Zharov et al., "In vivo photoacoustic flow cytometry for monitoring of circulating single cancer cells and contrast agents", Optics Letters, 2006, pp. 3623-3625, vol. 31, No. 24.
Zou et al., "BOLD response to visual stimulation in survivors of childhood cancer", NeuroImage, 2005, pp. 61-69, vol. 24.
Al et al., "Spectral-domain optical coherence tomography: Removal of autocorrelation using an optical switch", Applied Physics Letters, 2006, pp. 111115-1-111115-3, vol. 88.
Allen et al., "Pulsed near-infrared laser diode excitation system for biomedical photoacoustic imaging", Optics Letters, 2006, pp. 3462-3464, vol. 31, No. 23.
Bell, "On the Production and Reproduction of Sound by Light", American Journal of Sciences, Third Series, Oct. 1880, pp. 305-324, vol. XX.
Calasso et al., "Photoacoustic Point Source", Physical Review Letters, 2001, pp. 3550-3553, vol. 86, No. 16.
Cannata et al., "Development of a 35-MHz Piezo-Composite Ultrasound Array for Medical Imaging", IEEE Transactions on Ultrasonics, Ferroelectrics, and Frequency Control, 2006, pp. 224-236, vol. 53, No. 1.
Cheong et al., "A Review of the Optical Properties of Biological Tissues", IEEE Journal of Quantum Electronics, 1990, pp. 2166-2185, vol. 26, No. 12.
D'Andrea et al., "Time-resolved optical imaging through turbid media using a fast data acquisition system based on a gated CCD camera", Journal of Physics D: Applied Physics, 2003, pp. 1675-1681, vol. 36.
de Boer et al., "Improved signal-to-noise ratio in spectral-domain compared with time-domain optical coherence tomography", Optics Letters, 2003, pp. 2067-2069, vol. 28, No. 21.
Diebold et al., "Photoacoustic "Signatures" of Particulate Matter: Optical Production of Acoustic Monopole Radiation", Science, New Series, 1990, pp. 101-104, vol. 250, No. 4977.
Diebold et al., "Photoacoustic Monopole Radiation in One, Two, and Three Dimensions", Physical Review Letters, 1991, pp. 3384-3387 and FIGS. 1 and 2, vol. 26, No. 24.
Dunn et al., "Transport-based image reconstruction in turbid media with small source-detector separations", Optics Letters, 2000, pp. 1777-1779, vol. 25, No. 24.
Ermilov et al., "Laser optoacoustic imaging system for detection of breast cancer", Journal of Biomedical Optics, 2009, pp. 024007 1-024007 14, vol. 14, No. 2.
Erpelding et al., "Sentinel Lymph Nodes in the Rat: Noninvasive Photoacoustic and US Imaging with a Clinical US System", Radiology, 2010, pp. 102-110, vol. 256, No. 1.
Extended European Search Report from European Patent Application No. 08842292.8, dated Dec. 17, 2013, 8 pgs.
Fan et al., "Development of a laser photothermoacoustic frequency-swept system for subsurface imaging: Theory and experiment", J. Acoust. Soc. Am., 2004, pp. 3523-3533, vol. 116, No. 6.
Fang et al., "Photoacoustic Doppler Effect from Flowing Small Light-Absorbing Particles", Physical Review Letters, 2007, pp. 184501 1-184501 4, vol. 99.
Fercher et al., "Measurement of intraocular distances by backscattering spectral interferometry", Optics Communications, 1995, pp. 43-48, vol. 117.
Foster et al., "Advances in Ultrasound Biomicroscopy", Ultrasound in Medicine and Biology, 2000, pp. 1-27, vol. 26, No. 1.
Gibson et al., "Recent advances in diffuse optical imaging", Physics in Medicine and Biology, 2005, pp. R1-R43, vol. 50.
Guittet et al., "In Vivo High-Frequency Ultrasonic Characterization of Human Dermis", IEEE Transactions on Biomedical Engineering, 1999, pp. 740-746, vol. 46, No. 6.
Hebden et al., "Enhanced time-resolved imaging with a diffusion model of photon transport", Optics Letters, 1994, pp. 311-313, vol. 19, No. 5.
Hee et al., "Femtosecond transillumination tomography in thick tissues", Optics Letters, 1993, pp. 1107-1109, vol. 18, No. 13.

Hillman et al., "Laminar optical tomography: demonstration of millimeter-scale depth-resolved imaging in turbid media", Optics Letters, 2004, pp. 1650-1652, vol. 29, No. 14.
Hoelen et al., "Three-dimensional photoacoustic imaging of blood vessels in tissue", Optics Letters, 1998, pp. 648-650, vol. 23, No. 8.
Hu et al., "Label-free photoacoustic ophthalmic angiography", Optics Letters, 2010, pp. 1-3, vol. 35, No. 1.
Huang et al., "Optical Coherence Tomography", Science, New Series, 1991, pp. 1178-1181, vol. 254, No. 5035.
Huber et al., "Three-dimensional and C-mode OCT imaging with a compact, frequency swept laser source at 1300 nm", Optics Express, 2005, pp. 10523-10538, vol. 13, No. 26.
ISR and Written Opinion from related International Application No. PCT/US2008/081167, dated Apr. 22, 2009; 7 pgs.
ISR and Written Opinion from related International Application No. PCT/US2009/061435, dated Mar. 29, 2010; 10 pgs.
ISR and Written Opinion from related International Application No. PCT/US2011/022253, dated Sep. 22, 2011; 8 pgs.
ISR and Written Opinion from related International Application No. PCT/US2011/031823, dated Dec. 26, 2011; 8 pgs.
ISR and Written Opinion from related International Application No. PCT/US2012/068403, dated Mar. 19, 2013; 10 pgs.
Karamata et al., "Multiple scattering in optical coherence tomography. I. Investigation and modeling", Journal Optical Society of America, 2005, pp. 1369-1379, vol. 22, No. 7.
Kim et al., "In Vivo Molecular Photoacoustic Tomography of Melanomas Targeted by Bioconjugated Gold Nanocages", Acs Nano, 2010, pp. 4559-4564, vol. 4, No. 8.
Kolkman et al., "In Vivo Photoacoustic Imaging of Blood Vessels Using an Extreme-Narrow Aperture Sensor", IEEE Journal of Selected Topics in Quantum Electronics, 2003, pp. 343-346, vol. 9, No. 2.
Kruger et al., "Photoacoustic ultrasound (PAUS)—Reconstruction tomography", Med. Phys., 1995, pp. 1605-1609, vol. 22, No. 10.
Kruger et al., "Thermoacoustic computed tomography—technical considerations", Medical Physics, 1999, pp. 1832-1837, vol. 26, No. 9.
Kruger et al., "Breast Cancer in Vivo: Contrast Enhancement with Thermoacoustic CT at 434 MHz—Feasibility Study", Radiology, 2000, pp. 279-283, vol. 216, No. 1.
Kruger et al., "Thermoacoustic computed tomography using a conventional linear transducer array", Medical Physics, 2003, pp. 856-860, vol. 30, No. 5.
Kruger et al., "Thermoacoustic Optical Molecular Imaging of Small Animals", Molecular Imaging, 2003, pp. 113-123, vol. 2.
Ku et al., "Scanning thermoacoustic tomography in biological tissue", Medical Physics, 2000, pp. 1195-1202, vol. 27, No. 5.
Ku et al., "Scanning microwave-induced thermoacoustic tomography: Signal, resolution, and contrast", Medical Physics, 2001, pp. 4-10, vol. 28, No. 1.
Ku et al., "Multiple-bandwidth photoacoustic tomography", Physics. Med. Biol., 2004, pp. 1329-1338, vol. 49, No. 7.
Ku et al., "Deeply penetrating photoacoustic tomography in biological tissues enhanced with an optical contrast agent", Optics Letters, 2005, pp. 507-509, vol. 30, No. 5.
Ku et al., "Imaging of tumor angiogenesis in rat brains in vivo by photoacoustic tomography", Applied Optics, 2005, pp. 770-775, vol. 44, No. 5.
Ku et al., "Thermoacoustic and Photoacoustic Tomography of Thick Biological Tissues Toward Breast Imaging", Technology in Cancer Research & Treatment, 2005, pp. 559-566, vol. 4, No. 5.
Leitgeb et al., "Performance of fourier domain vs. time domain optical coherence tomography", Optics Express, 2003, pp. 889-894, vol. 11, No. 8.
Li et al., "Optical coherence computed tomography", Applied Physics Letters, 2007, pp. 141107-1-141107-3, vol. 91.
Li et al., "Simultaneous Molecular and Hypoxia Imaging of Brain Tumors In Vivo Using Spectroscopic Photoacoustic Tomography", Proceedings of the IEEE, 2008, pp. 481-489, vol. 96, No. 3.
Manohar et al., "Initial Results of in vivo non-invasive cancer imaging in the human breast using near-infrared photoacoustics", Optics Express, 2007, pp. 12277-12285, vol. 15, No. 19.

(56) References Cited

OTHER PUBLICATIONS

Maslov et al., "In vivo dark-field reflection-mode photoacoustic microscopy", Optics Letters, 2005, pp. 625-627, vol. 30, No. 6.
Maslov et al., "Photoacoustic imaging of biological tissue with intensity-modulated continuous-wave laser", Journal of Biomedical Optics, 2008, pp. 024006 1-024006 5, vol. 13, No. 2.
Maslov et al., "Optical-resolution photoacoustic microscopy for in vivo imaging of single capillaries", Optical Letters, 2008, pp. 929-931, vol. 33, No. 9.
Mishra et al., "Development and comparison of the DTM, the DOM and the FVM formulations for the short-pulse laser transport through a participating medium", International Journal of Heat and Mass Transfer, 2006, pp. 1820-1832, vol. 49.
Morgner et al., "Spectroscopic optical coherence tomography", Optics Letters, 2000, pp. 111-113, vol. 25, No. 2.
Murray et al., "High-sensitivity laser-based acoustic microscopy using a modulated excitation source", Applied Physics Letters, 2004, pp. 2974-2976, vol. 85, No. 14.
Nakajima et al., "Three-Dimensional Analysis and Classification of Arteries in the Skin and Subcutaneous Adipofascial Tissue by Computer Graphics Imaging", Plastic and Reconstructive Surgery, 1998, pp. 748-760, vol. 102, No. 3.
Nelson et al., "Imaging Glioblastoma Multiforme", The Cancer Journal, 2003, pp. 134-145, vol. 9, No. 2.
Niederhauser et al., "Combined Ultrasound and Optoacoustic System for Real-Time High-Contrast Vascular Imaging in Vivo", IEEE Transactions on Medical Imaging, 2005, pp. 436-440, vol. 24, No. 4.
Office Action from related U.S. Appl. No. 13/574,994, dated Aug. 26, 2014; 10 pgs.
Office Action from related U.S. Appl. No. 13/574,994, dated Mar. 17, 2014; 9 pgs.
Notice of Allowance from related U.S. Appl. No. 12/739,589, dated Feb. 5, 2013; 9 pgs.
Office Action from related U.S. Appl. No. 12/739,589, dated Jul. 19, 2012; 9 pgs.
Notice of Allowance from related U.S. Appl. No. 12/254,643, dated Nov. 22, 2010; 8 pgs.
Office Action from related U.S. Appl. No. 12/254,643, dated Aug. 6, 2010; 9 pgs.
Notice of Allowance from related U.S. Appl. No. 13/369,558, dated Jul. 29, 2014; 7 pgs.
Office Action from related U.S. Appl. No. 13/369,558, dated Jun. 20, 2014; 10 pgs.
Office Action from related U.S. Appl. No. 11/625,099, dated Nov. 1, 2010; 11 pgs.
Office Action from related U.S. Appl. No. 11/625,099, dated Apr. 20, 2010; 11 pgs.
Office Action from related U.S. Appl. No. 13/450,793, dated Aug. 1, 2014; 21 pgs.
Office Action from related U.S. Appl. No. 13/450,793, dated Jun. 5, 2013; 20 pgs.
Office Action from related U.S. Appl. No. 13/637,897, dated Aug. 1, 2014; 7 pgs.
Notice of Allowance from related U.S. Appl. No. 12/568,069, dated Feb. 22, 2013; 7 pgs.
Office Action from related U.S. Appl. No. 12/568,069, dated Dec. 21, 2012; 10 pgs.
Office Action from related U.S. Appl. No. 12/568,069, dated Sep. 18, 2012; 14 pgs.
Office Action from related U.S. Appl. No. 12/568,069, dated Mar. 29, 2012; 10 pgs.
Office Action from related U.S. Appl. No. 13/125,522, dated Jul. 17, 2014; 10 pgs.
Office Action from related U.S. Appl. No. 13/125,522, dated May 23, 2013; 10 pgs.
Office Action from related U.S. Appl. No. 13/125,522, dated Jan. 22, 2013; 8 pgs.
Oraevsky et al., "Laser Opto-Acoustic Imaging of the Breast: Detection of Cancer Angiogenesis", Proc. SPIE, 1999, pp. 352-363, vol. 3597, No. 56.
Oraevsky et al., "Ultimate Sensitivity of Time-Resolved Opto-Acoustic Detection", Biomedical Optoacoustics, Proceedings of SPIE, 2000, pp. 228-239, vol. 3916.
Oraevsky et al., "Optoacoustic Tomography", Biomedical Photonics Handbook, 2003, pp. 1-40, CRC Press LLC, USA.
Petrov et al., "Optoacoustic, Noninvasive, Real-Time, Continuous Monitoring of Cerebral Blood Oxygenation: An In Vivo Study in Sheep", Anesthesiology, 2005, pp. 69-75, vol. 102, No. 1.
Potter et al., "Capillary Diameter and Geometry in Cardiac and Skeletal Muscle Studied by Means of Corrosion Casts", Microvascular Research, 1983, pp. 68-84, vol. 25.
Robert et al., "Fabrication of focused poly (vinylidene fluoride-trifluoroethylene) P (VDF-TrFE) copolymer 40-50 MHz ultrasound transducers on curved surfaces", Journal of Applied Physics, 2004, pp. 252-256, vol. 96, No. 1.
Saager et al., "Direct characterization and removal of interfering absorption trends in two-layer turbid media", J. Opt. Soc. Am. A, 2005, pp. 1874-1882, vol. 22, No. 9.
Schmidt et al., "A 32-channel time-resolved instrument for medical optical tomography", Review of Scientific Instruments, 2000, pp. 256-265, vol. 71, No. 1.
Schroeter et al., "Spontaneous slow hemodynamic oscillations are impaired in cerebral microangiopathy", Journal of Cerebral Blood Flow & Metabolism, 2005, pp. 1675-1684, vol. 25.
Sheth et al., "Columnar Specificity of Microvascular Oxygenation and Volume Responses: Implications for Functional Brain Mapping", The Journal of Neuroscience, 2004, pp. 634-641, vol. 24, No. 3.
Shmueli et al., "Low-frequency fluctuations in the cardiac rate as a source of variance in the resting-state fMRI BOLD signal", NeuroImage, 2007, pp. 306-320, vol. 38.

* cited by examiner

MINIATURIZED PHOTOACOUSTIC IMAGING APPARATUS INCLUDING A ROTATABLE REFLECTOR

CROSS REFERENCE TO RELATED APPLICATIONS

This application is a 35 U.S.C. §371 national stage application of PCT/US2010/020488, filed Jan. 8, 2010, which claims the benefit of U.S. Provisional Patent Application No. 61/143,668 filed Jan. 9, 2009, the entireties of which are hereby incorporated by reference for all purposes.

STATEMENT REGARDING FEDERALLY SPONSORED RESEARCH & DEVELOPMENT

This invention was made with government support under grant R01 NS46214, awarded by the U.S. National Institutes of Health. The government has certain rights in the invention.

BACKGROUND

The embodiments described herein relate generally to endoscopic scanning methods and apparatus and, more particularly, to a photoacoustic endoscope that enables both photoacoustic imaging and ultrasonic imaging through the use of a rotatable reflector, such as a prism or a mirror.

Photoacoustic microscopy or computed tomography is an emerging imaging modality that has much potential for in vivo structural and functional imaging of biological tissues. It can produce spectroscopic optical absorption-based contrast images in optically scattering media such as human tissue while maintaining high spatial resolution (up to approximately 10 μm). In addition to the intrinsic contrast, by employing other biocompatible molecular contrast agents, such as organic dyes, quantum dots, or nano-particles, lesions can be profiled with molecular contrasts at high resolution.

Photoacoustic waves are generated by the instant thermal stress of biological tissue induced by an external energy supply, typically through a laser pulse although radiofrequency or microwave pulses may also be used. Even with weak light illumination, less than the ANSI safety limit (20 mJ/cm$^2$ per laser pulse), detectable acoustic waves can be generated by the photoacoustic phenomenon, and cross-sectional or volumetric images of internal structures can be reconstructed by moving the illumination and detection points over the region of interest. To acquire the photoacoustic signal, typically a light delivering unit, a signal detection unit including an ultrasonic transducer, and a mechanical scanning unit are employed.

BRIEF DESCRIPTION

In one aspect, a reflection-mode photoacoustic endoscope is provided, including a light source configured to emit a light pulse, a signal detection or transmission unit configured to receive or emit an ultrasonic pulse, and a rotatable or scanning reflector configured to reflect the light pulse and the ultrasonic pulse into a target area of an object, and reflect a response signal to the signal detection unit. The response signal is one of a photoacoustic wave generated by the object responsive to the light pulse and an ultrasonic pulse echo generated by the object responsive to the ultrasonic pulse.

In another aspect, an endoscopy system is provided, including a reflection-mode photoacoustic endoscope, a data-acquisition system, and a data-analysis computer. The endoscope includes a light source configured to emit a light pulse, a signal detection or transmission unit configured to receive or emit an ultrasonic pulse, and a rotatable reflector configured to reflect the light pulse and the ultrasonic pulse into a target area of an object, and reflect a response signal to the signal detection unit. The response signal is one of a photoacoustic wave generated by the object responsive to the light pulse and an ultrasonic echo generated by the object responsive to the ultrasonic pulse. The data-acquisition system is configured to receive an electronic signal generated by the signal detection unit based on the response signal, and the data-analysis computer is configured to generate an image based on the electronic signal.

In another aspect, an endoscopy scanning method includes emitting a pulse, reflecting the pulse into an object using a rotatable mirror such that a response signal is emitted by the object responsive to the incident pulse, and reflecting the response signal, by the mirror, to a signal detection unit. The pulse is one of a light pulse and an ultrasonic pulse, and the response signal is one of a photoacoustic wave generated by the object in response to the light pulse and an ultrasonic echo generated by the object in response to the ultrasonic pulse. The method also includes generating an electronic signal based on the response signal, and generating an image based on the electronic signal.

BRIEF DESCRIPTION OF THE DRAWINGS

The embodiments described herein may be better understood by referring to the following description in conjunction with the accompanying drawings.

DETAILED DESCRIPTION

Figure 1:
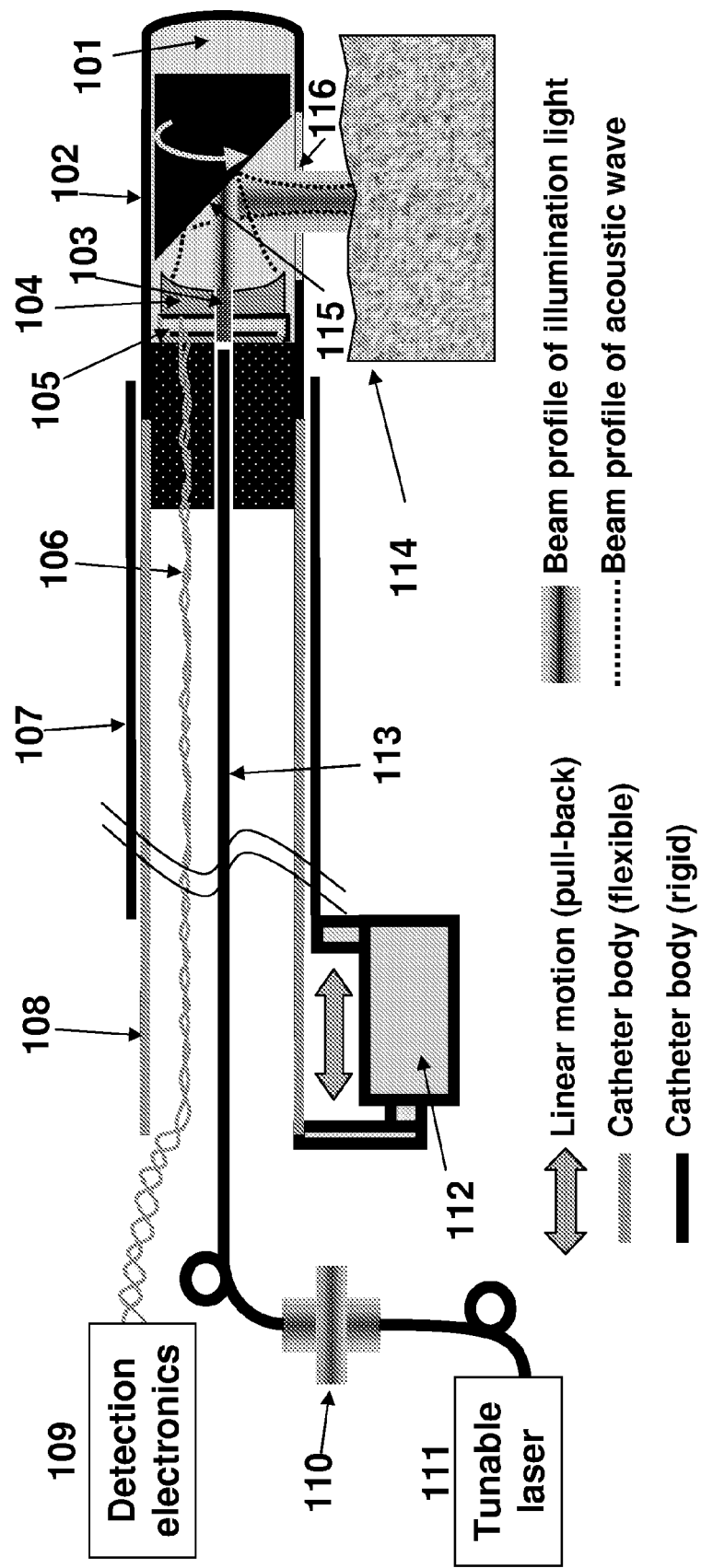
FIG. 1 is a diagram showing a general scanning concept of a photoacoustic endoscope that employs a rotatable mirror.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of the embodiments described herein, a number of terms are defined below. The terms defined herein have meanings as commonly understood by a person of ordinary skill in the areas relevant to the present invention. Terms such as "a," "an," and "the" are not intended to refer to only a singular entity, but rather include the general class of which a specific example may be used for illustration. The terminology herein is used to describe specific embodiments of the invention, but their usage does not delimit the invention, except as outlined in the claims.

To be consistent with the commonly used terminology, whenever possible, the terms used herein will follow the definitions recommended by the Optical Society of America (OCIS codes).

In some embodiments, the term "photoacoustic microscopy" refers generally to a photoacoustic imaging technology that detects pressure waves generated by light absorption in the volume of a material (such as biological tissue) and propagated to the surface of the material. In other words, photoacoustic microscopy is a method for obtaining three-dimensional images of the optical contrast of a material by detecting acoustic or pressure waves traveling from the object. The emphasis is on the micrometer scale image resolution.

In some embodiments, the term "photoacoustic tomography" also refers to a photoacoustic imaging technology that detects acoustic or pressure waves generated by light absorption in the volume of a material (such as biological tissue) and propagated to the surface of the material. The emphasis is sometimes on photoacoustic computed tomography, i.e., cross-sectional or three-dimensional photoacoustic imaging based on computer reconstruction, although the most general definition of photoacoustic tomography encompasses photoacoustic microscopy.

In some embodiments, the term "ultrasonography" refers generally to the conventional ultrasound pulse-echo imaging.

In some embodiments, the term "reflection mode" refers generally to the operation mode of a photoacoustic imaging system that detects pressure waves transmitted from the volume of their generation to the optical irradiation surface.

In some embodiments, the term "pulse-echo mode" refers generally to a scanning mode used to acquire A-line signals by detecting the amplitude of the backscattered echoes versus the time after transmission of the ultrasound pulse.

In some embodiments, the term "dark-field illumination" refers generally to an illumination method in photoacoustic microscopy, which is the opposite of bright-field illumination. By illuminating a target tissue at a low angle from the side, over a broad area having an annular shape, strong photoacoustic signal generation from the superficial surface above the focal zone of acoustic lens may be avoided or minimized.

In some embodiments, the term "photoacoustic waves" refers generally to pressure waves produced by light absorption.

In some embodiments, the term "time-resolved detection" refers generally to the recording of the time history of a pressure wave.

In some embodiments, the term "A-line" ("A" stands for amplitude) originates from the terminology of traditional ultrasonography, and it refers generally to a one-dimensional image along the depth direction. Here, the A-line is plotted with the acquired time-resolved photoacoustic signals versus the time after the launch of the light pulses.

In some embodiments, the term "B-scan" or "B-mode" ("B" stands for brightness) refers generally to a mechanical or electronic scanning mode that produces a two-dimensional image showing a cross section of tissue. Each line perpendicular to the scanning direction in the image represents an A-line, with the brightness of the signal being proportional to the amplitude of the photoacoustic signal.

In some embodiments, the term "piezoelectric detector" refers generally to detectors of acoustic waves utilizing the principle of electric charge generation upon a change of volume within crystals subjected to a pressure wave.

In some embodiments, the term "transducer array" refers generally to an array of ultrasonic transducers.

In some embodiments, the terms "focused ultrasonic detector," "focused ultrasonic transducer," and "focused piezoelectric transducer" refer generally to a curved ultrasonic transducer with a hemispherical surface or a planar ultrasonic transducer with an acoustic lens attached or an electronically focused ultrasonic array transducer.

In some embodiments, the terms "transducer array" and "phase array transducer" refer generally to an array of piezoelectric ultrasonic transducers.

In some embodiments, the term "mirror" refers generally to any device capable of deflecting propagation axis light and/or ultrasound. Such a device may include a metal or dielectric angle mirror, off-axis spherical or parabolic mirror, prism, lens, or any combination thereof.

Minimally invasive tissue diagnosis via an endoscope has shown broad applicability in the medical imaging field. Ultrasonography based imaging catheters have become widely used, and have shown robust performance independently or in combination with video endoscopes. Unlike the video endoscope, ultrasonographic endoscopes enable the diagnosis of deeper areas of the organ wall. However, they have relatively poor contrast and are thus not best suited, for example, for detecting early stage cancer. To overcome this shortcoming, optical imaging modalities have been developed and are attracting much attention due to their advantages in contrast, safety, and portability. Recent studies have shown their potential and superiority over conventional ultrasonography in the early diagnosis of cancerous tissue. The endoscopic optical coherence tomographic (OCT) imaging technique shows much potential in terms of optical contrast and resolution. This technique also has the advantage of realizing a very tiny catheter probe with high scanning speed. However, its poor imaging depth (less than 1 mm) still remains a major limitation.

In at least some known medical imaging, optical modalities provide an optical contrast image. However, such optical modalities are fundamentally limited to poor spatial resolution at depths greater than one transport mean free path (e.g., ~1 mm in most biological tissues) due to high optical scattering in tissue. For example, diffuse optical tomography (DOT) may produce tomographic images reaching regions up to several centimeters deep, but it is very poor in spatial resolution because diffused (scattered) light is employed. A main application for DOT is imaging the human brain and/or breast. However, DOT is inappropriate for endoscopic applications.

Further examples are endoscopic optical techniques that employ ballistic or quasi-ballistic photons, such as confocal endoscopy. Endoscopic optical and optical coherence tomographic (OCT) probes having various components and scanning mechanisms have been reported. However, while such techniques and/or probes are capable of imaging small objects with high resolution, they are still unsatisfactory in detecting cancerous tissue developed deeper than one transport mean free path below the surface.

In addition, ultrasonography may also be miniaturized for endoscopic diagnosis. This imaging modality takes advantage of high resolution and deep penetration characteristics of ultrasonic waves. Owing to the low scattering of ultrasound, compared to that of light in biological tissue, deep imaging may be achieved. During scanning, pulsed ultrasonic waves are sent to a region of interest, and reflected waves, or echoes, are recorded and reconstructed as a cross-sectional, e.g., B-scan, image or as a 3-D volumetric image. However, this technique has insufficient contrast because the mechanical properties of the early-stage abnormal tissue differ little from those of normal tissue.

Photoacoustic imaging modalities capitalize on two domains, i.e., imaging of optical contrast through light illumination, and deep imaging with high resolution by employing photoacoustically induced ultrasonic waves. For this reason, photoacoustic imaging technology is considered one of the most promising imaging modalities for biomedical applications. Its endoscopic realization in particular can make significant contributions to the medical imaging field.

In realizing a catheter probe for photoacoustic endoscopy, the size restriction is a most challenging issue. Among known endoscopic imaging modalities, two imaging systems are representative and related to the embodiments described herein. The first is an ultrasonic endoscopic catheter, and the second is an optical catheter probe employing optical coherence tomography. The ultrasonic endoscopic catheter captures a reflected signal from a region of interest after sending an ultrasonic pulse, which is referred to as the pulse-echo mode. The optical catheter probe employs a backscattered optical signal from a focused illumination. In order to produce a circular B-scan image, both systems use circumferential sector scanning, or radial scanning, with a scanning element, such as a focused ultrasonic transducer or optical lens, attached at the tip of a flexible shaft. If necessary, linear motion of the scanning element, which is referred to as pullback, may be accomplished manually or automatically to acquire successive B-scan images, which are necessary for volumetric image composition. The required mechanical driving force is typically transmitted from the proximal end through a flexible shaft embedded in the inner part of the catheter. The electrical signal from the ultrasonic transducer (in the case of endoscopic ultrasonography) or the optical signal (in the case of endoscopic OCT) from the optical lens is transferred to the signal-receiving center through electromagnetic or optical coupling at the proximal end and finally reconstructed as a B-scan or volumetric image. This is the most widely utilized scanning mechanism because it can be fabricated with a very simple structure in restricted space. Such endoscopic probes can work separately as intravascular probes or jointed with video endoscopes through the instrument channels. In addition, such a scanner shows robust performance in terms of scanning speed, e.g., more than 30 Hz frame rate for B-scan, as well as flexibility in advancing toward the region of interest in the tissue. However, in using endoscopic probes, it is technically difficult to transmit both the impulse energy, whether the energy is an optical or electrical pulse, and the resultant response signal from a target through the rotating proximal end. This disjointed transmission mechanism deteriorates signal stability during rotational motion and worsens the signal-to-noise ratio as well. This issue would become more serious in a photoacoustic endoscope system because the induced signal from the photoacoustic phenomenon is weaker than that of conventional ultrasonographic endoscopes using the pulse-echo method. For this reason, more stable light delivery and photoacoustic signal transfer during scanning are essential in realizing the system. Additionally, the relatively high stiffness of the flexible shaft limits the endoscope's abilities, e.g., maneuverability, in imaging delicate tissues. Hereinafter, embodiments of a scanning mechanism and system configuration for the effective embodiment of a photoacoustic endoscope are disclosed.

Addressing this limitation, the embodiments described herein provide a photoacoustic endoscope, which is a hybrid imaging modality combining the strengths of two domains, optics and ultrasound. Since it is capable of producing optical absorption-based contrast images at challenging depths (1-5 mm) with high spatial resolution, it is superior in screening suspicious tissue at deeper regions. Moreover, the described system in accordance with the current invention is capable of producing double contrast images having different origins, i.e., an optical absorption based image and a pure ultrasound image based on the tissue's acoustic properties. The spectral behavior of optical absorption in the region of interest enables analysis of metabolism and offers rich information concerning the tissue. In addition, when used with appropriate biochemical markers for a specific disease, the embodiments described herein facilitate identifying tissue abnormalities more clearly.

The embodiments described herein may be used in the diagnosis of various tissue lesions that develop in internal organs. Its applicability lies in various organs and many duct structures, such as the lungs, esophagus, gastrointestinal tract, colon, or blood vessels. Most of all, it is expected to be especially useful in screening cancerous tissues, such as myogenic tumors of the esophagus, gastric cancer, pancreatic cancer, colon cancer and carcinoma of the common bile duct. Needless to say, in addition to its medical applications for human welfare, it can be applied to various types of animal study for research purposes.

Figure 9:
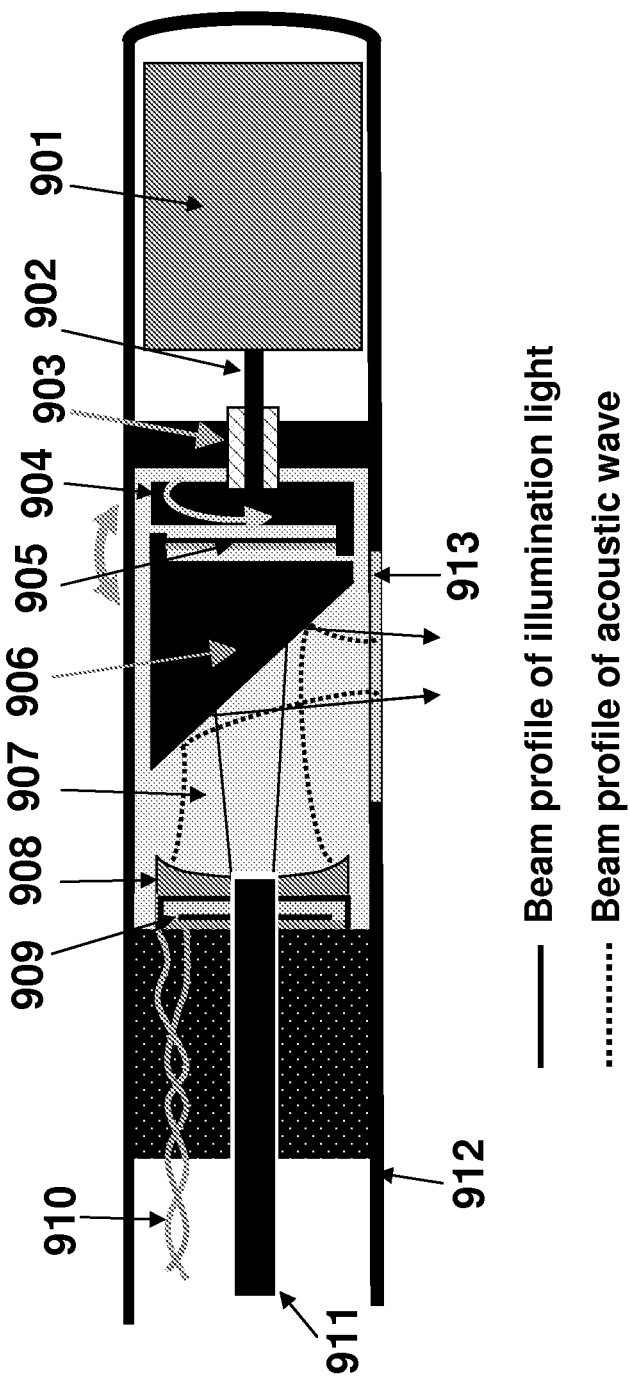
FIG. 9 is a diagram showing a different mechanical scanning mode to perform 3D imaging of the target tissue, in which a bending actuator is employed to steer both the illumination zone and the ultrasonic focal point of the scanning mirror.
Figure 10:
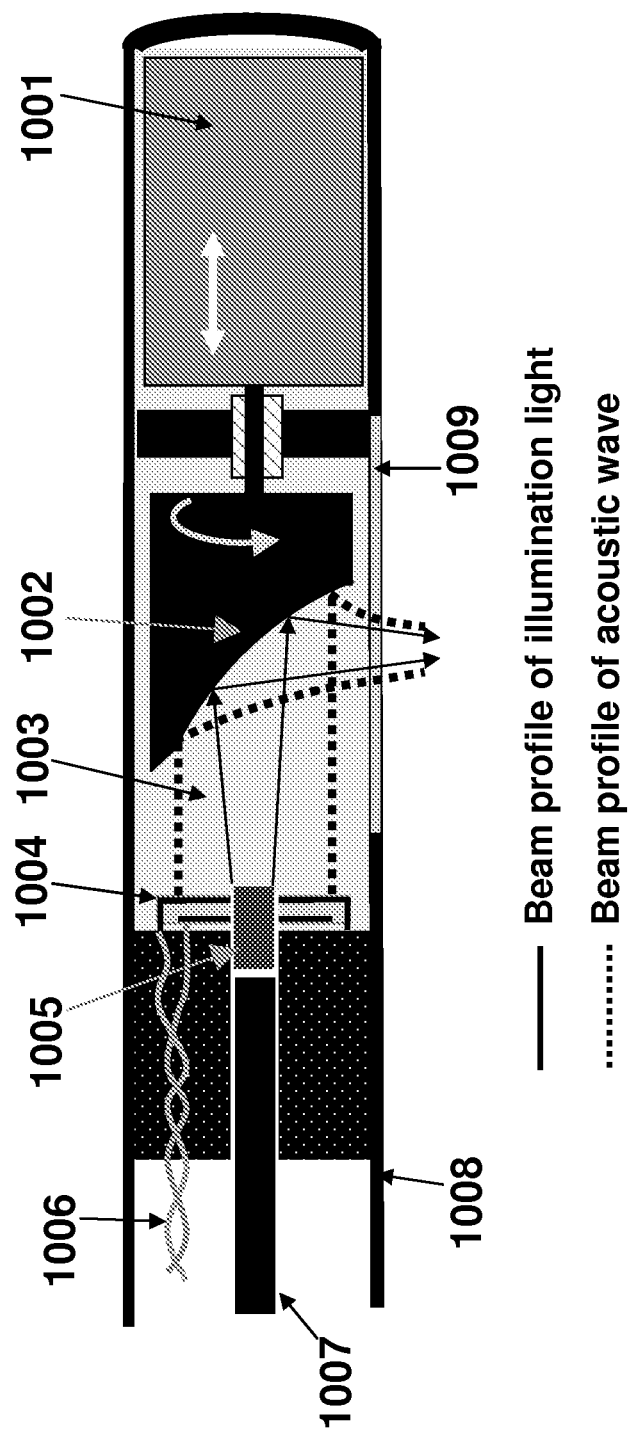
FIG. 10 is a diagram showing another mechanical scanning mode to perform 3D imaging of the target tissue, in which a translational freedom of the parabolic mirror is allowed in addition to the rotational scanning.

FIG. 1 is a schematic illustration of a general concept of a scanning mechanism and system configuration of a reflection-mode photoacoustic endoscope. In the exemplary embodiment, the endoscope includes an illumination unit 103 that provides light illumination of a target area, a mechanical scanning unit employing a scanning mirror 115, and a signal detection unit that includes an ultrasonic transducer 105 and an acoustic lens 104. Scanning mirror 115 reflects not only light but also ultrasonic waves, as a mechanical scanning substitute. Unlike a universal ultrasonographic endoscope, the photoacoustic endoscope here does not directly rotate the ultrasonic detection elements 104 and 105 but, rather, rotates the scanning mirror 115 instead to achieve scanning over the region of interest. One or more light pulses are guided from an external light source (e.g., a pulse laser) 111 through an optical fiber 113 via coupling optics 110 and the proximal end to the illumination unit 103 located at the distal end. The optimal duration of the light pulse varies with the targeted resolution and can vary on the order of approximately 1.0 nanosecond (ns) to approximately 1.0 microsecond (p), wherein the shorter the duration, the higher the spatial resolution. Light emitted from the outlet of the illumination unit 103 is reflected from the surface of the scanning mirror 115 and transmitted to the tissue surface 114 at the point of aim via an optically transparent or translucent membrane 116, i.e., an imaging window. Strong optical scattering of biological tissue homogenizes the illumination in relatively deep tissue. For light pulses of a short duration, tissue temperature rise caused by light energy absorption is confined to the volume of the absorptive target during the light pulse, and the resultant photoacoustic pressure waves are generated in proportion to the optical fluence $\Phi$ (J/m$^2$), and the absorption coefficient $\mu_a$ (cm$^{-1}$) of the irradiated area. Some of the acoustic waves pass through via the imaging window 116, are reflected by the scanning mirror 115, and are captured by the ultrasonic transducer 105 through the acoustic lens 104. The ultrasonic transducer 105 converts the photoacoustic wave pressure into a time-resolved electric signal and transmits it to the detection electronics 109 through electric signal wires 106 that extend along the catheter body 108. This mechanism can detect a single A-line signal. By repeating this process during the movement of the scanning mirror 115, a set of data for planar or volumetric imaging can be collected. Virtually, various kinds of motion, such as rotational, translation, alternating, etc., are possible for the scanning mirror 115. Representatively, a B-scan image can be acquired through the rotational motion of the scanning mirror 115 like the conventional scanning mode of ultrasonographic endoscopes. A volumetric image can be formed as a composition of serial B-scan images consecutively acquired during the linear motion of the scanning mirror 115. Here, two kinds of scanning mode are supposable for the linear scanning. The first mode is to pull back the whole endoscope probe, which can be achieved manually or by a linear actuator 112 connected to the proximal end of the catheter body 108. This method follows the conventional scanning mode and is applicable to any embodiment of the photoacoustic endoscope system described herein. The second mode is to translate only the scanning mirror 115 inside the distal end while the catheter body 108 remains static (as shown in FIG. 10). The second scanning method is more appropriate for small area scanning compared to the conventional pull-back method but superior in terms of contact stability. In addition to the translational scanning mode for the scanning mirror 115, a tilted scanning mode can be employed to produce a volumetric image (as shown in FIG. 9). To secure smooth pull-back motion of the probe in the instrument channel of a co-operating video endoscope, another tube, such as an outer tube 107, may be added to the sheath of the catheter body 108 in order to avoid direct contact between the catheter and the inner wall of the instrument channel. In addition, the catheter body may also be formed in two sections having different materials: a flexible tube 108 for the proximal and middle part of the body, and a rigid tube 102 for the distal part, if stable optical alignment is necessary to the optical components in the distal part. In the illumination unit 103, the single strand of fiber 113 may be employed alone for the light illumination, without adding other optical components. In this case, the illumination zone will be broad and is determined by the numerical aperture and the diameter of the fiber 113. Other optical components may be added to the outlet of the fiber 113 to increase the tightness of the illumination zone. By illuminating target tissue more tightly, photoacoustic waves may be induced from a more selected area. The required mechanical torque for rotating the scanning mirror 115 may be supplied directly by an embedded source or indirectly by an external source through a suitable transmission method, such as a flexible driving shaft.

Such a configuration facilitates stable light delivery and stable signal detection, which means improvement of the SNR. Because the illumination optics 103 and ultrasonic detection element 105 (with the acoustic lens 104) do not participate in the mechanical scanning but remain static, possible technical issues in disjointed rotating coupling, i.e., light transfer to and signal reception from the proximal end of the rotating flexible shaft, may be avoided. Here, "static" does not mean the preclusion of the movement of the elements with the whole probe system. Rather, "static" means no relative movement in the distal end. Additionally, since this scanning mechanism does not preclude traditional pure ultrasonic imaging capability, i.e., pulse-echo mode, two forms of imaging can be performed and automatically co-registered for side-by-side displays and/or overlays. This scanning mechanism's simple structure permits fabrication of a tiny endoscopic probe, one small enough to perform not only independently but also with existing gastrointestinal fiber scopes through their instrument channels.

Since the mirror's oblique reflection surface serves as a signal transmitter as well as a scanning substitute, its surface must be made with an appropriate material for both light and ultrasonic wave reflection. From basic acoustic theory, one of ordinary skill in the art should understand that ultrasound rays, both longitudinal rays and shear rays, approaching the reflection surface of high acoustic impedance material at a large incidence angle are highly or totally reflected. Because of the high acoustic impedance difference between the scanning mirror 115 and its background medium (i.e., immersion medium) 101, the ultrasonic reflection from the mirror 115 is high even at small incidence angles. Therefore, the acoustic wave reflection mechanism of the present invention, i.e., using a scanning mirror having an oblique reflection surface, facilitates providing satisfactory propagation of ultrasonic waves, which is comparable to the conventional ultrasonographic endoscope system that directly rotates the detection element. In the exemplary embodiment, the inner part of the distal end is filled with an acoustically transparent liquid medium 101, such as water or mineral oil, to provide an acoustic impedance matching medium for ultrasonic wave propagation. In addition, in the exemplary embodiment, the optically transparent imaging window 116 is made with an ultrasound permeable material, and its area is determined according to its specific application. Instead of attaching an acoustic lens 104 having a concave surface to the ultrasonic transducer 105, the reflection surface of the scanning mirror 115 may be formed as a curved shape like a concave optical mirror to focus ultrasonic waves. In some embodiments, the scanning mirror 115 is formed with a parabolic shape in order to minimize aberration. In the exemplary embodiment, an array of ultrasonic transducers may replace the acoustic lens 104 and provide spatial focusing capability using synthetic aperture imaging. The ultrasonic sensing element 105 may be composed of various materials, forms, and/or types, such as piezo-polymer or piezoceramic, focused or unfocused, and single element or an array of many elements. It is desirable to have broad bandwidth for achieving high axial resolution. Typical endoscopic ultrasonographic imaging frequencies range from a few megahertz (MHz) to approximately 100.0 MHz. A PVDF film based transducer is also good for acoustic wave detection. In addition, optical detection methods, such as the Fabry-Perot interferometery, may replace the conventional piezoelectric effect based transducers. In some embodiments, in order to increase the electric signal transmission efficiency from the ultrasonic transducer 105 to the detection electronics 109, a preamplifier circuit is embedded into the catheter tube near the ultrasonic transducer 105.

Figure 2:
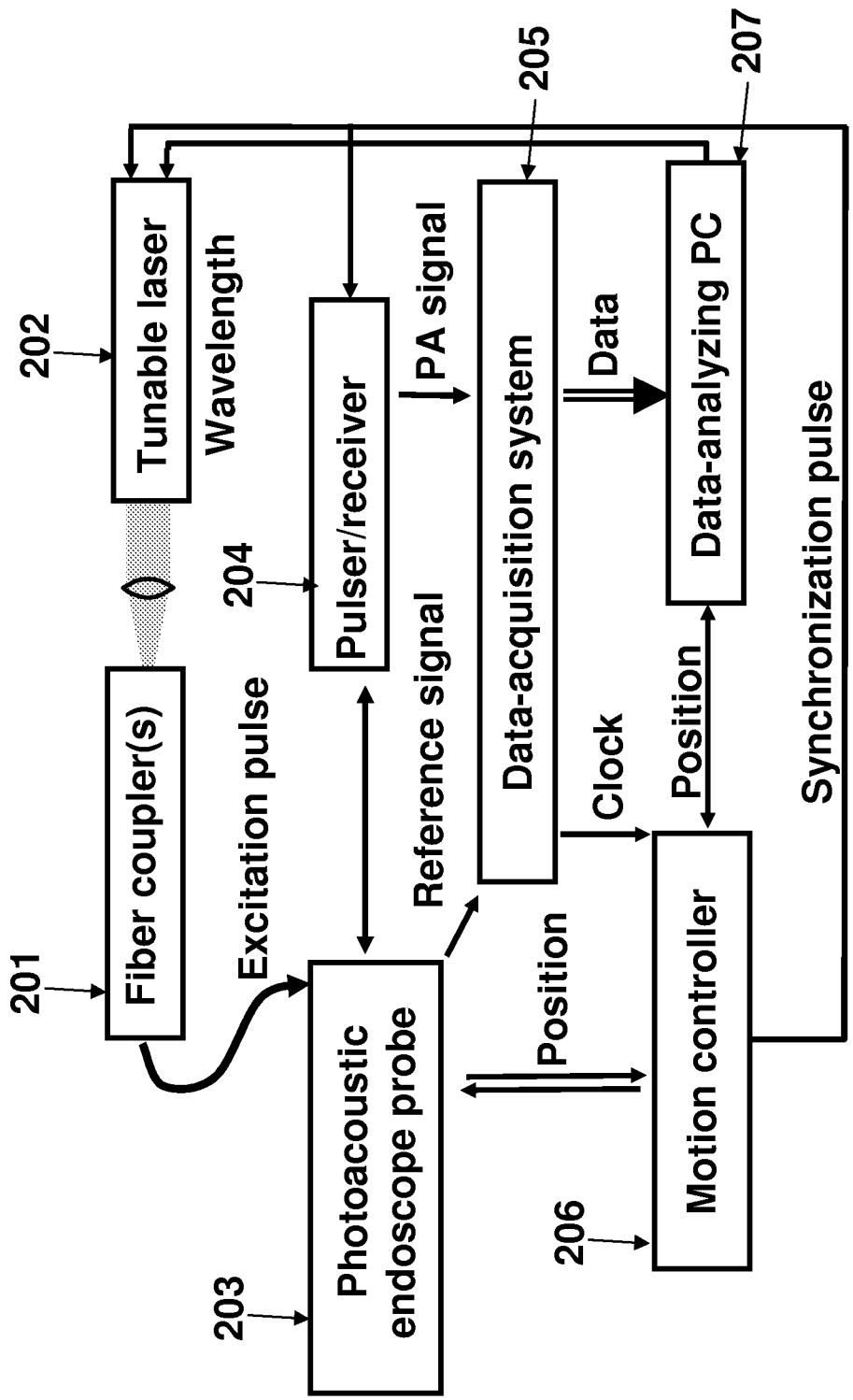
FIG. 2 is a block diagram showing the photoacoustic endoscope probe and its peripheral systems.

FIG. 2 is a block diagram of the photoacoustic endoscope probe shown in FIG. 1 and its peripheral system. The system includes a light source and light delivery subsystem that consists of a tunable pulse laser 202, an optical fiber or fibers and associated fiber coupling optics 201, a photoacoustic endoscope probe 203, and a detection electronic subsystem that may include an ultrasonic pulser/receiver 204, a motion controller 206, a data-acquisition system 205, and/or a data-analyzing PC 207. Laser pulses from a pulse laser 202 (e.g., a tunable dye laser or diode lasers) are used to illuminate the tissue. The laser's wavelength is selected to obtain specific spectral image information. A set of time-resolved photoacoustic signals generated by the laser pulse is captured by the data acquisition system 205 during a set time interval. In some embodiments, the data-acquisition system 205 is a digital oscilloscope system, data acquisition computer board, and/or a stand alone digitizer having a high sampling rate. A time-resolved photoacoustic signal produced by a single laser pulse forms an A-line that contains optical absorption and depth information. A cross-sectional (B-scan) image is formed with a series of A-line signals acquired during the circumferential rotation of the scanning mirror. The rotation of the scanning mirror 115 (shown in FIG. 1) and the pull-back of the linear actuator 112 (shown in FIG. 1) are controlled by the motion controller 206, and its position information is communicated to the data-analyzing PC 207. Through real time data communication among the data-acquisition system 205, the motion controller 206, and/or the data-analyzing PC 207, cross-sectional (B-scan) or volumetric images are composed and displayed promptly by installed image reconstruction software. By setting the pulser/receiver 204 accordingly, the ultrasonic transducers may work alternatively in two modes. In a first mode, the ultrasonic transducers work as a receiving transducer for photoacoustic imaging. In a second mode, the ultrasonic transducers work as a pulser/receiver for conventional pulse-echo mode ultrasonic imaging. The data-acquisition subsystem 205 produces a clock signal to synchronize all electronic subsystems.

Maintaining the aforementioned scanning concept shown in FIG. 1, an example of a mechanism for transmitting driving force to the scanning mirror 115, with one of several possible configurations of associated elements at the distal end according to the present invention, will be described by referring to FIG. 3. One of ordinary skill in the art should understand that there may be many methods for transmitting the driving force, so this example does not restrict the scope of the present invention, but merely provides an exemplary embodiment of the scanning concept. This embodiment is more focused on the conventional circumferential scanning capability for real time circular B-mode image display. Components shown in FIG. 3, identical to components shown in FIGS. 1 and 2, are identified in FIG. 3 using the same reference numerals used in FIGS. 1 and 2.

Figure 3:
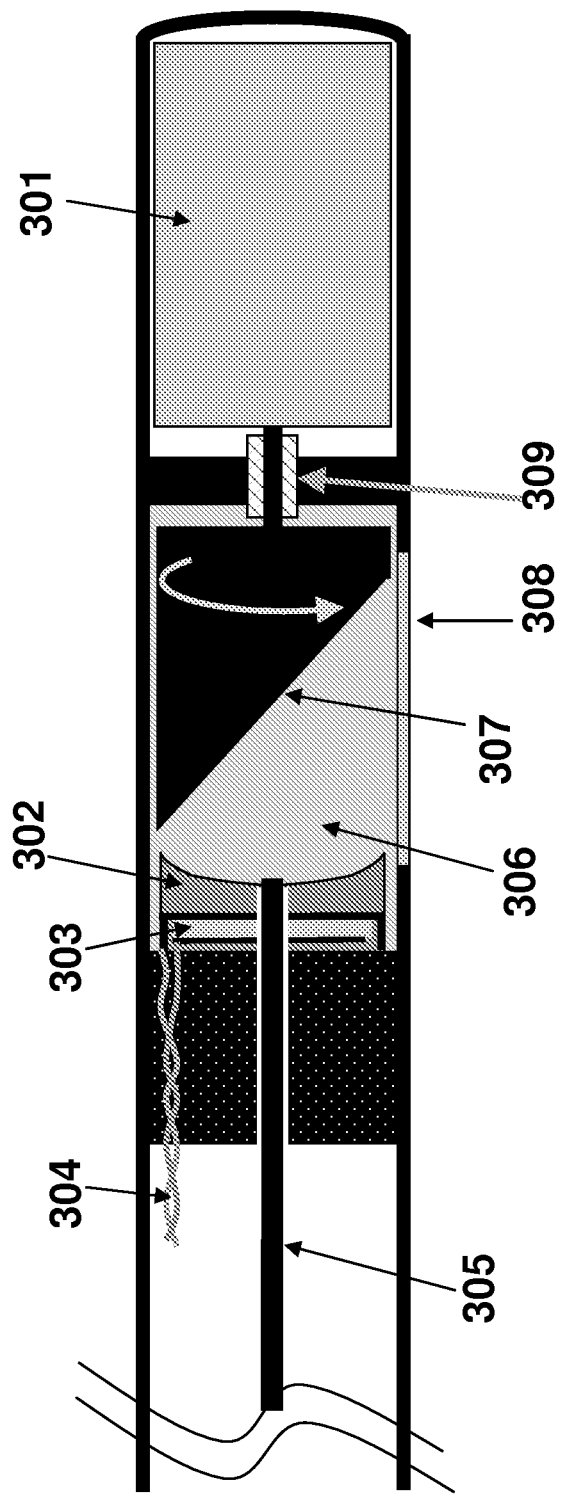
FIG. 3 is a diagram of a representative embodiment showing a miniature electric motor (micromotor) based scanning mechanism according to the general scanning concept shown in FIG. 1.

FIG. 3, unlike a universal ultrasonographic endoscope employing an external driving force through a flexible shaft for rotating the scanning tip, is a schematic diagram of an photoacoustic endoscope that includes a micromotor 301, which is small enough to satisfy the general instrument channel size constraint, e.g., approximately 2.7 millimeters (mm) in diameter, of universal gastrointestinal fiber scopes, for rotation. During the light illumination with optical fiber 305, the circumferential sector scanning is performed by the scanning mirror 307 that receives torque from the micromotor 301. Generated photoacoustic signals coming from the imaging window 308 are captured by the ultrasonic transducer 303 through the acoustic lens 302, converted into an electric signal, and transferred to the detection electronics 109 (shown in FIG. 1) through electric wires 304. In some embodiments, the motor's housing space is sealed from the immersion medium 306 because commercially available micromotors are designed for an in-air working environment. Moreover, a couple of small bearings 309, such as jewel bearings, may be used to provide smooth mirror rotation and seal the interface between the two compartments. Alternatively, a waterproof micromotor or other actuators, such as a direct drive brushless motor, designed to work under water may be utilized. The current method employing a micromotor 301 provides an adequate frame rate of the B-scan image, determined by the rotational speed of the micromotor. Using an existing micromotor providing enough torque to turn the scanning mirror 307, an approximately 30.0 Hz frame rate is achievable. A frame rate of approximately 30.0 Hz is the typical frame rate of a universal ultrasonographic endoscope probe. The frame rate is adjustable by using an appropriate gear assembly with the micromotor 301. In addition to the rotational speed of the motor, the pulse repetition rate of the laser is a factor that determines the angular image resolution in a radial B-scan image. Recent laser systems can achieve high repetition rates, up to a few kHz.

The micromotor based scanning mechanism has several advantages over the conventional method utilizing a flexible shaft. It improves catheter flexibility, which means better maneuverability, and does not require rotational coupling of optical and electric signals thus improves the SNR of the system. Moreover, any kink in the endoscope's body would not affect the scanning mirror's movement, and a phase delay in the rotation of the scanning mirror would not occur, but it might when a flexible shaft is employed. In various embodiments, the configuration of the required elements may be varied for specific applications, as described hereinbelow.

The current system provides photoacoustic and conventional ultrasonic imaging simultaneously according to the aforementioned method and may be used for diagnostic, monitoring, or research purposes. In addition, this scanning mechanism and related imaging systems according to the present invention may replace or complement conventional planar (both in x and y-direction) scanning mode based photoacoustic imaging systems. The scanning mechanism may be realized as a co-operating probe with a video endoscope system, being small enough to be pulled through the instrument channel (around 2.7 mm) of the video endoscope. In addition, the current photoacoustic endoscope system may be used for diagnosis independently as a specialized gastro-endoscope or recto-scope. In this case, the probe diameter is equal or close to the body size of conventional video endoscopes, around 10 mm in diameter. Such a probe may incorporate an ultrasound preamplifier for improving SNR, angulation capability for probe steering, and a CCD camera for transmitting visual information during it maneuvers. To provide stable contact conditions between the endoscope and target tissues, the balloon contact or water immersion methods may be employed.

The main applications of the technology include, but are not limited to, in vivo imaging and diagnosis of various kinds of cancerous tissues in the gastrointestinal tract and plaques in blood vessels of humans. The present invention may use the spectral properties of intrinsic optical contrast to monitor blood oxygenation (oxygen saturation of hemoglobin), blood volume (total hemoglobin concentration), and/or the metabolic rate of oxygen consumption, which is referred to as functional imaging. It may also use the spectral properties of a variety of dyes or other contrast agents to obtain additional functional or molecular-specific information, i.e., molecular imaging. Since the acoustic property based contrast image supplied by the pure ultrasonic imaging capability is produced together with the photoacoustic image, plenty of diagnostic information may be provided to a practitioner synergistically.

Figure 4:
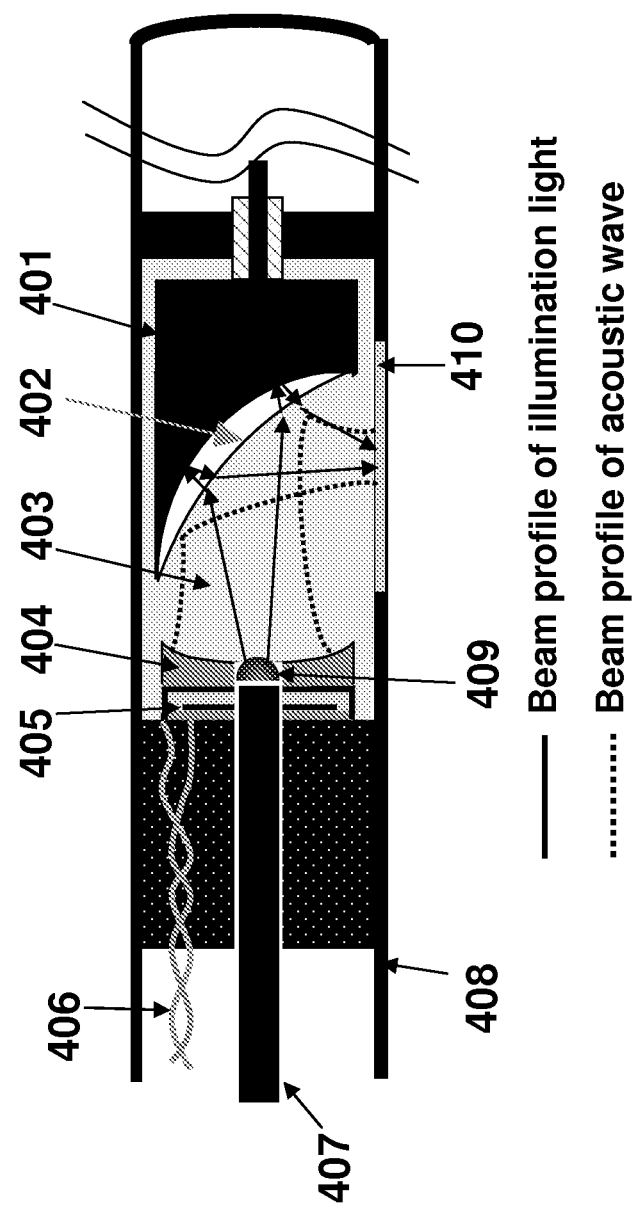
FIG. 4 is a diagram of an alternative embodiment of the optical illumination unit and ultrasonic detection element, employing a meniscus reflector to focus both illumination and detection more tightly.
Figure 5:
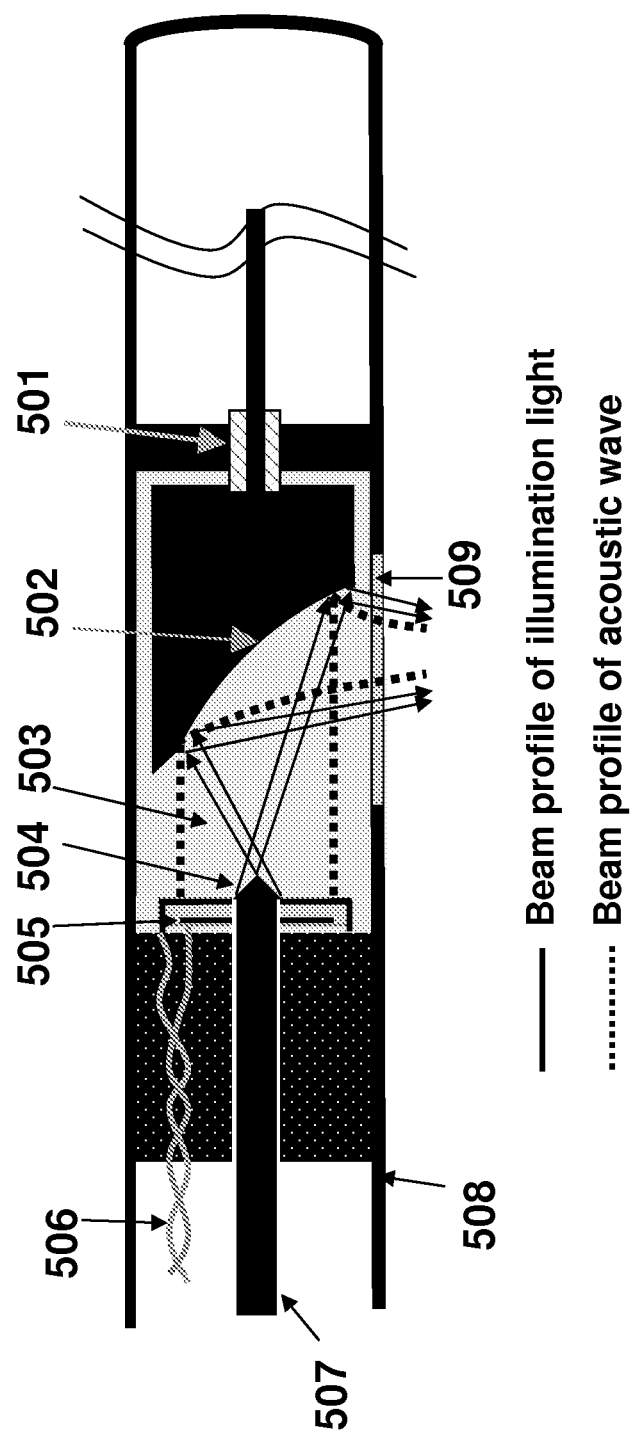
FIG. 5 is a diagram of an alternative embodiment of the optical illumination unit and ultrasonic detection element, where a conical lens and a parabolic mirror are employed for darkfield illumination and tight focusing of ultrasonic waves, respectively.

Using the optical fiber illumination method shown in FIG. 3, even without other optical components, a sufficiently tiny illumination zone may be formed at the surface of the target tissue, provided that an optical fiber having a low numerical aperture is employed. However, the illumination unit may also be configured as a more integrated optics system to focus light more tightly at the target point. In some embodiments, the illumination unit includes an optical assembly of lenses, prisms, and/or mirrors. There also could be some variation in placing the outlet of the illumination unit, at the central position as shown in FIG. 3, or at the circumference of the ultrasonic detection element. Similarly, the focal tightness of the ultrasonic detection element may be achieved by employing acoustic components, such as lenses and mirrors. The lateral resolution of the photoacoustic endoscope system is mainly determined by the ultrasonic focusing capability rather than the focal tightness of optical illumination in the quasi-diffusive or diffusive regime. Hence, a tighter focusing of the ultrasonic detection element with a higher numerical aperture may improve the image resolution and SNR. In FIGS. 4-5, various methods for more tight optical illumination and ultrasound focusing are described. Components shown in FIGS. 4 and/or 5, identical to components shown in FIGS. 1-3, are identified in FIGS. 4 and/or 5 using the same reference numerals used in FIGS. 1-3.

In FIG. 4, simple methods for more tight illumination of the target area as well as for more effective ultrasound focusing are provided. Here the scanning mirror having a flat surface 307 (shown in FIG. 3) is replaced with a curved shape mirror 402 having two reflection surfaces (i.e., meniscus) and is attached obliquely at the support 401. Two reflection surfaces provide focusing capabilities for light and/or ultrasound reflections, respectively. The back surface of the meniscus mirror 402 is coated with a light reflective material and provides a light reflection surface with a focusing capability like a conventional concave optical mirror. Similarly, the front surface of the meniscus mirror 402 is formed with a different curvature for ultrasonic wave reflection. Provided that the material of the meniscus mirror 402 has enough acoustic impedance difference to the background medium 403, most of the ultrasonic waves can be reflected by the front surface. Ultrasonic waves coming from the imaging window 410 are converged by the front surface and sent to the ultrasonic transducer 405 (and further transmitted to the detection electronics through signal wires 406 that extend along the catheter body 408). This ultrasound focusing capability can be achieved not only by the meniscus mirror 402 alone, but also by the acoustic lens 404 attached at the surface of the ultrasonic transducer 405. In addition, in some embodiments, a ball shape (or semi-ball shape) optical lens 409 may be added at the outlet of the optical fiber 407 to achieve more tight light illumination. By appropriately designing the curvatures of the two reflection surfaces of the meniscus mirror 402, the focal tightness of light illumination and ultrasound detection may be selectively determined, and ultrasonic aberration can be reduced.

In FIG. 5, different methods for light illumination of the target area, here referred to as a darkfield illumination, as well as for ultrasound focusing are provided. In this embodiment, an off-axis parabolic mirror 502 is employed for the scanning substitute and serves both light and ultrasound reflection. A small bearing 501, which may serve as a seal, provides smooth motion to the parabolic mirror 502. Provided that the material of the parabolic mirror 502 has enough acoustic impedance difference from the background medium 503, most of the ultrasonic waves are reflected by the front surface which also provides a reflection surface for light. Here, the curvature of the parabolic mirror 502 is determined to be more effective to the tight focusing of the ultrasonic waves rather than that of optical illumination. By a conical lens 504 attached at the outlet of the optical fiber 507, the laser beam coming out from the fiber 507 is formed as a hollow cone shaped beam and finally incident on the tissue surface with a ring-shaped broad illumination pattern after the reflection by the parabolic mirror 502. It is important that this dark-field illumination method suppresses strong photoacoustic signals from the tissue surface by decreasing the optical fluence at the central region of the ring-shaped illumination pattern. Under this illumination geometry, photoacoustic waves are dominantly generated at the focal zone that is formed at a deep region of the target tissue through the ring-shaped illumination. Some of the generated photoacoustic waves that propagate toward the parabolic mirror 502 via the imaging window 509 are reflected by the parabolic mirror 502 and finally detected by the ultrasonic transducer 505 (and further transmitted to the detection electronics through signal wires 506 that extend along the catheter body 508). Here, only the ultrasonic waves coming from a point source located at the off-axis focal point of the parabolic mirror 502 are converted into plane waves that propagate parallel to the normal of the flat ultrasonic transducer 505 and produce dominant piezoelectric signal to the transducer 505. Another important feature of the parabolic mirror-based detection configuration is that the numerical aperture of ultrasound detection is not affected by the distance between the parabolic mirror 502 and the ultrasonic transducer 505 but it is entirely determined by the distance between the parabolic mirror 502 and its focal point, and its area. So, one has the freedom in setting the distance between the mirror surface 502 and the ultrasonic transducer 505 while conserving the numerical aperture. Moreover, this ultrasound focusing mechanism employing the parabolic mirror 502 is superior to the spherical mirror in terms of aberration. These light/ultrasound focusing methods shown in FIGS. 4 and 5 may be applied to any system that is provided by the embodiments described herein.

Figure 6:
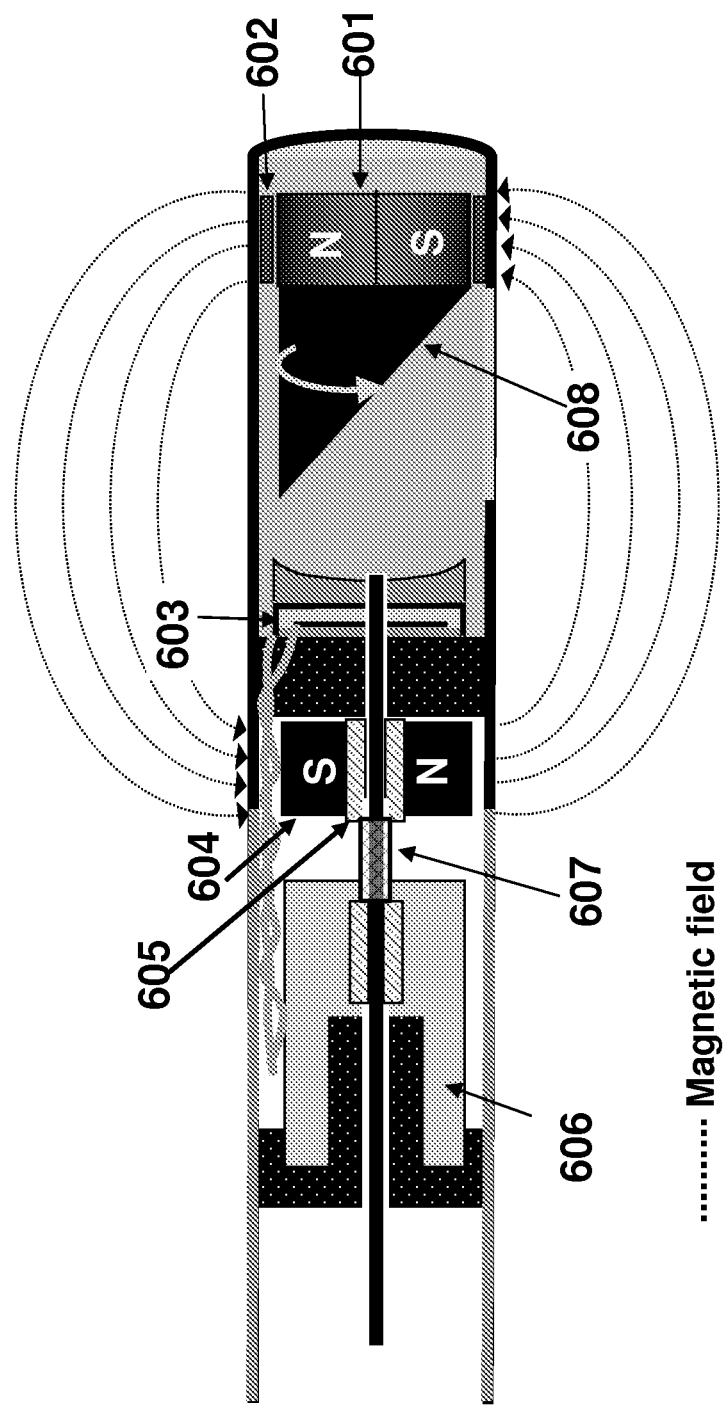
FIG. 6 is a diagram showing an alternative embodiment in the torque transmission to the scanning mirror at the distal end, where rotation is transferred via a magnetic coupling method from the micromotor.
Figure 7:
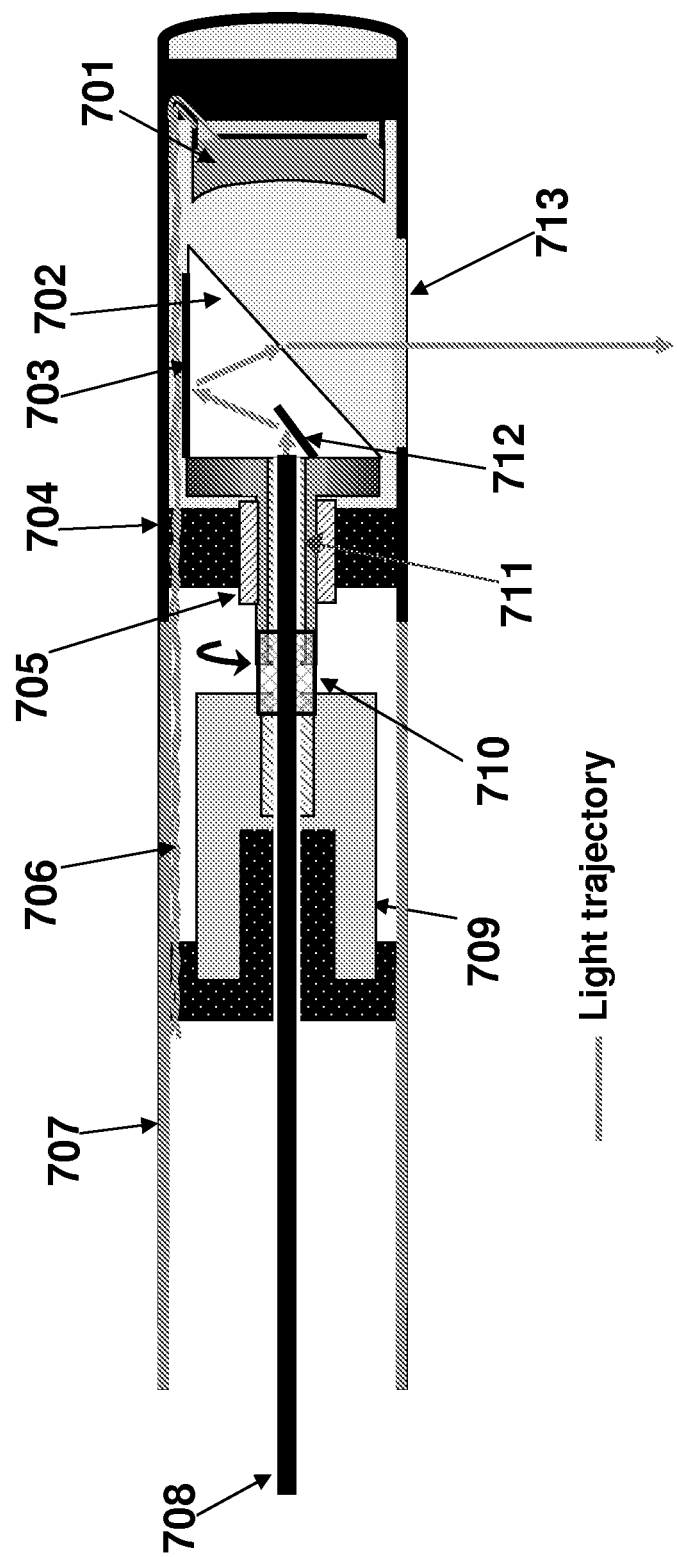
FIG. 7 is a diagram showing an alternative embodiment in the placement of the scanning reflector and the ultrasonic transducer at the distal end, while a micromotor is still employed for the driving force.
Figure 8:
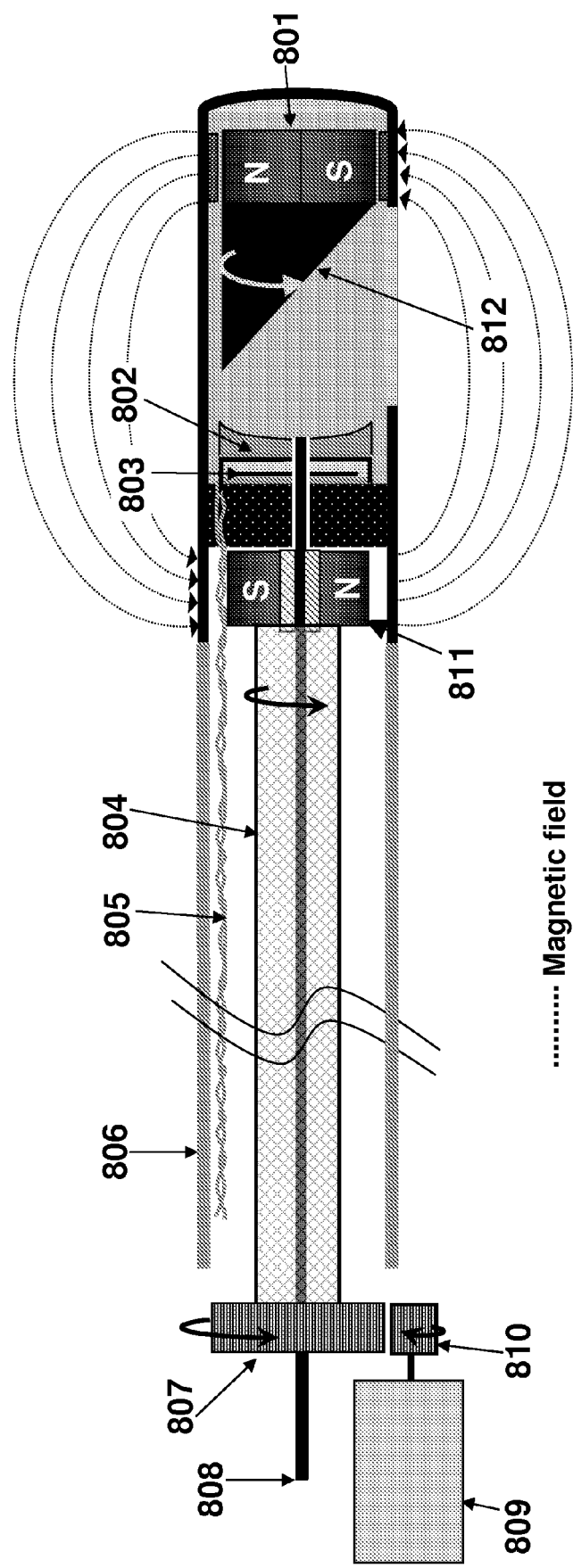
FIG. 8 is a diagram showing an alternative embodiment in the torque transmission to the scanning mirror at the distal end, in which a flexible shaft is employed for the transmission of the driving force from an external motor to the scanning mirror.

Preserving the basic scanning concept shown in FIG. 1, alternative embodiments on the driving force transmission mechanism to the scanning mirror and configurations of associated elements are provided in FIGS. 6-8. These embodiments are more oriented to the circumferential scanning capability of the scanning mirror and may be applied to such a circumstance that a short distance between the imaging window and the tip of the catheter is critical. Components shown in FIGS. 6-8, identical to components shown in FIGS. 1-5, are identified in FIGS. 6-8 using the same reference numerals used in FIGS. 1-5.

In FIG. 6, an embodiment in which the position of the micromotor 606 is moved from the distal end (shown in FIG. 3) to near the base of the ultrasonic transducer 603 is provided. In this case, the required torque of the scanning mirror 608 is transferred indirectly from the micromotor 606 through magnetic coupling. First the torque of the micromotor 606 is transferred to a magnet 604 through a flexible shaft 607, and further transmitted through the magnetic field to the opposite magnet 601 that is joined together with the scanning mirror 608. Finally, the scanning mirror 608 receives the torque and turns. Provided that sufficiently strong magnets are employed, the scanning mirror 608 rotates in step with the leading magnet 604. To secure the strong magnetic coupling, a non-magnetic material, such as plastic or stainless steel, is used for the surrounding material, e.g., the catheter body. Two small bearings 605 and 602 may be employed to provide smooth rotation of the leading magnet 604 and the opposite magnet 601. In addition, to reduce the coupling distance to the leading magnet 604, the whole of the mirror 608 may be fabricated with a magnetized material instead of attaching the additional magnet 601. Although the basic concept for the torque transmission shown in these examples is the magnetic coupling, other electromagnetic principles, such as electromagnetic induction, may be applied to transmit torque to the mirror. Moreover, the mechanical driving force employing the micromotor may be replaced with a hydraulic driving method.

In FIG. 7, an alternative embodiment in the position of the scanning mirror and the ultrasonic transducer is shown. Specifically, the positions of the scanning mirror and the ultrasonic transducer are reversed from the previous configuration shown in FIG. 6. This embodiment also utilizes the driving force generated by a micromotor 709, which is positioned in the flexible part of the catheter body 707. External light energy for illumination is guided to a tiny mirror 712 that is embedded in the scanning mirror (here, an optical prism) 702 though an optical fiber 708. The light is further guided by another tiny mirror 703 that is disposed in the prism 702 and is refracted at the prism's surface, then finally delivered to the target tissue. The two mirrors 703 and 712 rotate with the optical prism 702 that reflects ultrasonic waves during circumferential scanning; their torque is received from the micromotor 709. However, the optical fiber 708 remains static during their rotation. Two bearings 705 and 711 serve as mechanical interfaces that divide the rotating parts 702 from the static optical fiber 708 and play the role of sealing as well. To make the rigid section of the catheter body as short as possible, the micromotor 709 is placed in the flexible part 707 rather than the rigid part 704 of the catheter body. In addition, a flexible shaft 710 may be used to transfer the motor's torque. Generated photoacoustic signals coming via the imaging window 713 are detected by a focused ultrasonic transducer 701, and its electric signal is transferred to the detection electronics through signal wires 706.

In FIG. 8, another embodiment is provided that employs the magnetic coupling method shown in FIG. 6. However, this embodiment employs an external driving force through a flexible shaft. This configuration employing the flexible shaft would be more appropriate in circumstances where the flexibility of the catheter body is less critical. Like FIG. 6, a pair of magnets is employed, but the previous micromotor 606 (shown in FIG. 6) is replaced with an external motor 809. The torque generated by the external motor 809 is transferred to the leading magnet 811 through a flexible shaft 804 that extends inside the flexible catheter body 806. A gear 807 at the proximal end of the flexible shaft 804 is in gear engagement with a pinion 810 and receives torque from the external motor 809. In this configuration, since the optical fiber 808 embedded into the flexible shaft 804 remains static during the rotational motion of the flexible shaft 804 and the magnet 811, illumination light is delivered stably to the scanning mirror 812, precluding the coupling issue at the proximal end. The torque of the leading magnet 811 is transferred to the opposite magnet 801, such that the scanning mirror 812 receives the torque and performs circumferential scanning. Similar to the alternative mechanism shown in FIG. 6, generated photoacoustic waves are captured by the ultrasonic transducer 803 through an acoustic lens 802, and the electrically converted signals are transferred to the detection electronics through electric wires 805.

Preserving the basic system configuration and scanning mechanism shown in FIG. 1, two alternative types of mechanical scanning mode, which do not require the pull-back motion of the whole probe, are provided in FIGS. 9 and 10, to produce volumetric images. These scanning modes are more appropriate for small area scanning compared to the conventional pull-back method but superior in terms of scanning stability because the catheter body is kept stationary during the scanning.

In FIG. 9, a simple method for the 3D imaging of the target area is provided. In this embodiment, another scanning motion, i.e., a tilt motion (or a nodding motion), is allowed to the scanning mirror 906 in addition to its rotational motion. The scanning mirror 906 is attached to the support 904 via a bending actuator 905, which is made with a piezoceramic or a bimetal bimorph, in order to provide another scanning plane to the mirror 906. The tilt angle of the bending actuator 905 can be controlled dynamically by applying an appropriate voltage through the shaft 902 of the micromotor 901. In the exemplary embodiment, the micromotor 901 is fabricated as an integrated system that can supply a torque to the scanning mirror 906 and a voltage signal to the bending actuator 905 for the tilt motion. In some embodiments, the housing of the micromotor 901 is isolated from the background medium 907 by a seal (i.e., a jewel bearing) 903 if an in-air working environment is required. According to this scanning mechanism, the illumination zone and the ultrasonic focal point can be steered coincidentally over the region of interest. The emitted laser beam from the optical fiber 911 is reflected by the scanning mirror 906 and guided to the surface of the target tissue, finally generates ultrasonic waves. Some of the ultrasonic waves transmitted through the imaging window 913 are reflected by the scanning mirror 906, and propagated to the acoustic lens 908 and the ultrasonic transducer 909 (and further transmitted to the detection electronics through signal wires 910 that extend along the catheter body 912).

In FIG. 10, another scanning mode for the 3D imaging of the target area is provided. In this embodiment, the parabolic mirror 1002 is employed for the scanning substitute and obtains a translational freedom in conjunction with the rotational motion and performs linear scanning over the region of interest to produce volumetric images. The required torque and translational energy of the scanning mirror 1002 are supplied from a helical motion micromotor 1001, so the scanning point is moved linearly and/or circumferentially over the region of interest. As mentioned in FIG. 5, the parabolic surface of the scanning mirror 1002 converts the spherical ultrasonic waves coming from a point source, which is located at the off-axis focal point of the parabolic mirror 1002, via an imaging window 1009 into plane waves, and sends them to the flat ultrasonic transducer 1004. The acoustic pressure of the plane waves is converted into a piezoelectric signal by the flat ultrasonic transducer 1004 and transferred to the detection electronics through signal wires 1006 that extend along the catheter body 1008. However, it is important that the ultrasonic numerical aperture of the parabolic mirror 1002 does not change during the translational movement as mentioned in FIG. 5. In other words, the uniformity of ultrasonic signal detection may be secured even though the distance between the scanning mirror 1002 and the ultrasonic transducer 1004 changes. To secure illumination uniformity during the translational movement of the scanning mirror 1002, emitted beam from the illumination unit 1005 is formed as a collimated beam. For example, such a collimated beam may be achieved simply by employing an optical fiber 1007 having a low numerical aperture and an immersion medium having a high optical refractive index.

Figure 11:
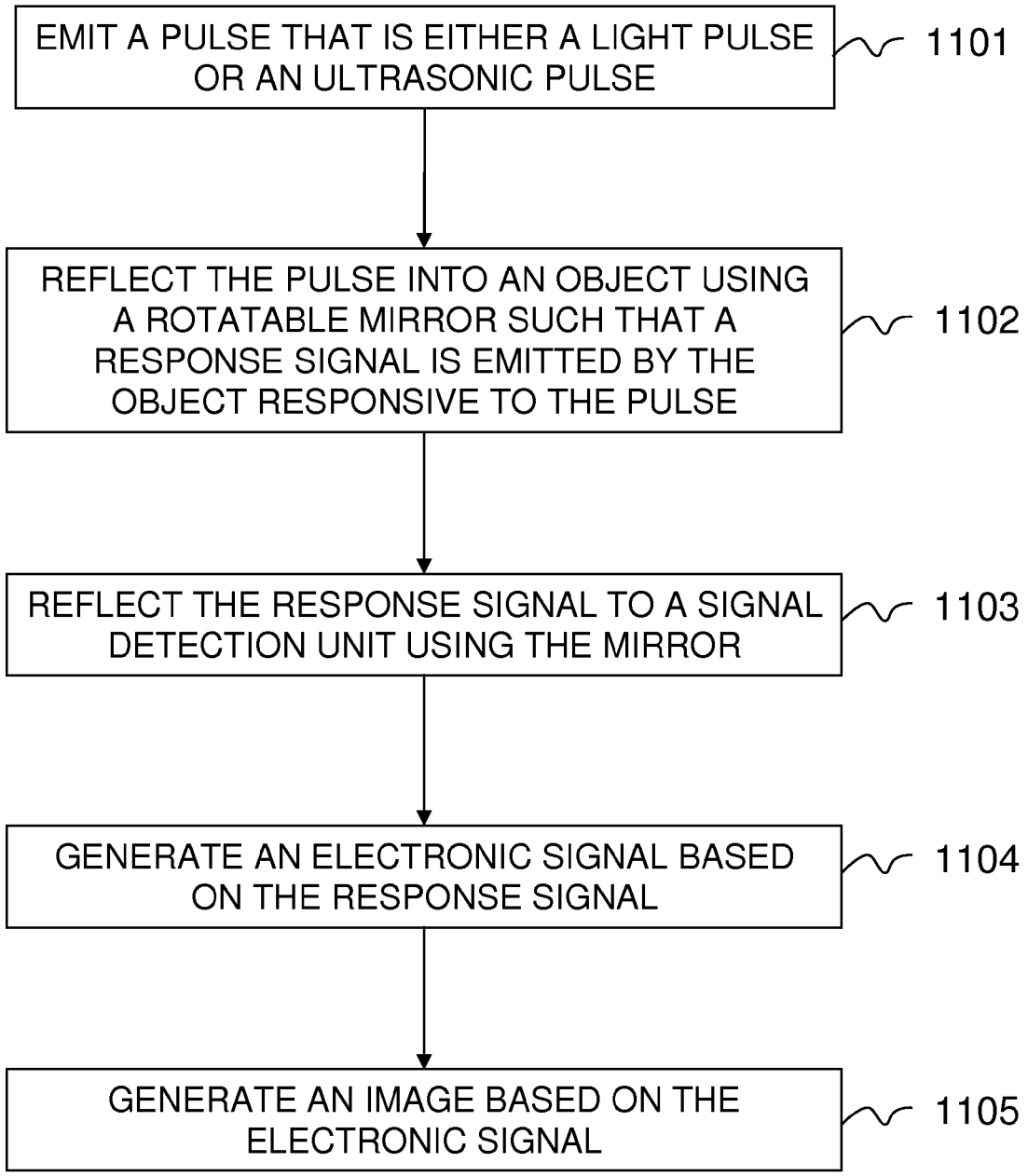
FIG. 11 is a flowchart illustrating an exemplary endoscopy scanning method using the photoacoustic endoscope concept shown in FIG. 1 and associated systems shown in FIG. 2.

FIG. 11 is a flowchart illustrating an exemplary endoscopy scanning method using the photoacoustic endoscope concept described above. Referring to FIGS. 1 and 2, and in the exemplary embodiment, a pulse is emitted 1101. The pulse may be a light pulse emitted by, for example, optical fiber 113. Alternatively, the pulse may be an ultrasonic pulse emitted by, for example, ultrasonic transducer 105. The pulse is then reflected 1102 by a rotatable mirror, such as mirror 115. More specifically, the pulse is reflected 1102 by the mirror 115 onto a target surface 114 of an object. In some embodiments, the mirror 115 is rotated by a micromotor, such as micromotor 301 (shown in FIG. 3). The micromotor 301 may include a plurality of gears or may be coupled to a gear mechanism, such as gear 807 (shown in FIG. 8). In some other embodiments, the mirror 115 is rotated by a micromotor that is coupled to a magnet assembly that includes a first magnet, such as magnet 604, and a second magnet, such as magnet 601 (both shown in FIG. 6).

In the exemplary embodiment, the pulse induces the object to emit a response signal. If the pulse signal is a light pulse, the response signal is a photoacoustic wave. Alternatively, if the pulse signal is an ultrasonic pulse, the response signal is an ultrasonic pulse echo. The response signal is reflected 1103 by the mirror 115 to a signal detection unit that includes, for example, an acoustic lens 104 and an ultrasonic transducer 105. The signal detection unit generates 1104 an electronic signal based on the response signal and transmits the electronic signal to a data-acquisition system 205. Finally, a data-analysis computer 207 generates 1105 an image based on the electronic signal, for display to an operator.

As enumerated before, possible configurations for realizing photoacoustic endoscope systems were provided according to the current invention. There may be further alternatives with minor modifications of the associated elements, in their number, size, position, or replacement with equivalents. In addition, basic ideas provided by the embodiments shown in FIGS. 1-10 on illumination, ultrasonic detection, and/or scanning mechanism may be utilized with the recombination for specific application. However, the basic scanning concept that employs the scanning mirror and associated operation of the mechanism should be maintained to maximize the stability of light delivery and photoacoustic signal transfer as described in this disclosure.

It will be understood that the particular embodiments described herein are shown by way of illustration and not as limitations of the invention. The principal features of this invention may be employed in various embodiments without departing from the scope of the invention. Those of ordinary skill in the art will recognize numerous equivalents to the specific procedures described herein. Such equivalents are considered to be within the scope of this invention and are covered by the claims.

All of the compositions and/or methods disclosed and claimed herein may be made and/or executed without undue experimentation in light of the present disclosure. While the compositions and methods of this invention have been described in terms of the embodiments included herein, it will be apparent to those of ordinary skill in the art that variations may be applied to the compositions and/or methods and in the steps or in the sequence of steps of the method described herein without departing from the concept, spirit, and scope of the invention. All such similar substitutes and modifications apparent to those skilled in the art are deemed to be within the spirit, scope, and concept of the invention as defined by the appended claims.

It will be understood by those of skill in the art that information and signals may be represented using any of a variety of different technologies and techniques (e.g., data, instructions, commands, information, signals, bits, symbols, and chips may be represented by voltages, currents, electromagnetic waves, magnetic fields or particles, optical fields or particles, or any combination thereof). Likewise, the various illustrative logical blocks, modules, circuits, and algorithm steps described herein may be implemented as electronic hardware, computer software, or combinations of both, depending on the application and functionality. Moreover, the various logical blocks, modules, and circuits described herein may be implemented or performed with a general purpose processor (e.g., microprocessor, conventional processor, controller, microcontroller, state machine or combination of computing devices), a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. Similarly, steps of a method or process described herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. Although preferred embodiments of the present invention have been described in detail, it will be understood by those skilled in the art that various modifications can be made therein without departing from the spirit and scope of the invention as set forth in the appended claims.

A controller, computing device, or computer, such as described herein, includes at least one or more processors or processing units and a system memory. The controller typically also includes at least some form of computer readable media. By way of example and not limitation, computer readable media may include computer storage media and communication media. Computer storage media may include volatile and nonvolatile, removable and non-removable media implemented in any method or technology that enables storage of information, such as computer readable instructions, data structures, program modules, or other data. Communication media typically embody computer readable instructions, data structures, program modules, or other data in a modulated data signal such as a carrier wave or other transport mechanism and include any information delivery media. Those skilled in the art should be familiar with the modulated data signal, which has one or more of its characteristics set or changed in such a manner as to encode information in the signal. Combinations of any of the above are also included within the scope of computer readable media.

The embodiments described herein relate to a concurrent optical excitation and ultrasonic detection that scans an object with motion of a single element (mirror). A mirror serves three purposes: it is a moving scanning substitute, and it reflects both light to be delivered to the target tissue and ultrasonic waves received from the target. It enables object scanning similarly to a universal catheterized medical imaging device while maintaining the illumination optics and ultrasonic detection element stationary. Additionally, the employment of a micromotor for the rotation of the scanning mirror and/or other active scanning techniques enables a more simplified system that eliminates flexible shafts thus improving catheter flexibility and does not use rotational coupling of optical and electric signals thus improving the signal to noise ratio of the system. The system effectively positions the required illumination optical unit and facilitates performing photoacoustic imaging as well as conventional pure ultrasonic imaging. It thereby enables production of double contrasts based on acoustic properties and optical absorption properties, making it desirable for the characterization of tissue abnormalities such as tumors. Similarly, pure optical imaging such as confocal microscopy and optical coherence tomography can be incorporated for multi-modality imaging. By utilizing a strong magnetic coupler with the micromotor, the required rotational force may be transmitted to the mirror effectively without direct mechanical connection, which enables diverse variations in the configuration of the components.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A reflection-mode photoacoustic endoscope comprising:
    a tube;
    a light source configured to emit a light pulse suitable for photoacoustic imaging;
    a signal detection or detection and transmission unit configured to detect or emit and detect an ultrasonic pulse; and
    a reflector rotatable relative to said tube and configured to:
        reflect the light pulse and the ultrasonic pulse into a target area of an object; and
        reflect a response signal to said signal detection unit, the response signal being one of a photoacoustic wave generated by the object responsive to the light pulse and an ultrasonic pulse echo generated by the object responsive to the ultrasonic pulse.

2. A reflection-mode photoacoustic endoscope in accordance with claim 1, further comprising a micromotor coupled at a first end to said reflector, said micromotor configured to impart a rotational force on said reflector.

3. A reflection-mode photoacoustic endoscope in accordance with claim 2, wherein said micromotor comprises a galvanometer lead.

4. A reflection-mode photoacoustic endoscope in accordance with claim 2, wherein said micromotor comprises a plurality of gears.

5. A reflection-mode photoacoustic endoscope in accordance with claim 2, wherein said micromotor is coupled at a second end to a gear mechanism.

6. A reflection-mode photoacoustic endoscope in accordance with claim 1, further comprising a micromotor and a magnet assembly, said magnet assembly coupled to said reflector.

7. A reflection-mode photoacoustic endoscope in accordance with claim 6, wherein said magnet assembly comprises a first magnet coupled to said micromotor and a second magnet positioned with respect to said first magnet and coupled to said reflector, said micromotor configured to generate torque, said first magnet configured to convert the torque into a magnetic field, said second magnet configured to rotate said reflector based on the magnetic field.

8. A reflection-mode photoacoustic endoscope in accordance with claim 1, wherein said signal detection unit comprises an ultrasonic transducer, said reflector comprises a parabolic mirror configured to reflect and focus the response signal onto said ultrasonic transducer.

9. A reflection-mode photoacoustic endoscope in accordance with claim 1, wherein said reflector comprises a plurality of reflective surfaces.

10. A reflection-mode photoacoustic endoscope in accordance with claim 1, wherein said endoscope is sized to fit within a catheter.

11. An endoscopy system comprising:
    a reflection-mode photoacoustic endoscope comprising:
        a tube;
        a light source configured to emit a light pulse suitable for photoacoustic imaging;
        a signal detection or transmission unit configured to detect or emit an ultrasonic pulse; and
        a mirror rotatable relative to said tube configured to reflect the light pulse and the ultrasonic pulse into a target area of an object, and reflect a response signal to said signal detection unit, the response signal being one of a photoacoustic wave generated by the object responsive to the light pulse and an ultrasonic pulse echo generated by the object responsive to the ultrasonic pulse;
    a data-acquisition system configured to receive an electronic signal generated by said signal detection unit based on the response signal; and
    a data-analysis computer configured to generate an image based on the electronic signal.

12. An endoscopy system in accordance with claim 11, wherein said endoscope further comprises a micromotor coupled at a first end to said mirror, said micromotor configured to impart a rotational force on said mirror.

13. An endoscopy system in accordance with claim 11, wherein said endoscope further comprises a micromotor and a magnet assembly, said magnet assembly coupled to said mirror.

14. An endoscopy system in accordance with claim 13, wherein said magnet assembly comprises a first magnet coupled to said micromotor and a second magnet positioned with respect to said first magnet and coupled to said mirror, said micromotor configured to generate torque, said first magnet configured to convert the torque into a magnetic field, said second magnet configured to rotate said mirror based on the magnetic field.

15. An endoscopy system in accordance with claim 11, wherein said signal detection unit comprises an ultrasonic transducer, said mirror comprises a parabolic mirror configured to reflect and focus the response signal onto said ultrasonic transducer.

16. An endoscopy system in accordance with claim 11, wherein said mirror comprises a plurality of reflective surfaces.

17. An endoscopy system in accordance with claim 11, wherein said endoscope is sized to fit within a catheter.

18. An endoscopy scanning method comprising:
    emitting a light pulse and an ultrasonic pulse;
    reflecting the pulses into an object using a mirror rotatable relative to a tube such that a response signals are emitted by the object responsive to the pulses;
    reflecting the response signals, by the mirror, to a signal detection unit, the response signals being a photoacoustic wave generated by the object in response to the light pulse and an ultrasonic pulse echo generated by the object in response to the ultrasonic pulse;

generating electronic signals based on the response signals; and generating an image based on the electronic signals.

19. An endoscopy scanning method in accordance with claim 18, further comprising rotating the mirror using a micromotor coupled to a plurality of gears.

20. An endoscopy scanning method in accordance with claim 18, further comprising rotating the mirror using a micromotor coupled to a magnet assembly.

* * * * *